US012618848B2

(12) United States Patent
Baaske et al.

(10) Patent No.: US 12,618,848 B2
(45) Date of Patent: May 5, 2026

(54) CHARACTERIZATION OF PARTICLES IN SOLUTION

(71) Applicant: Nanotemper Technologies GmbH, Munich (DE)

(72) Inventors: Philipp Baaske, Munich (DE); Jonathan Derix, Unterschleißheim (DE); Robert Haslinger, Eichenau (DE)

(73) Assignee: Nanotemper Technologies GmbH, Munich (DE)

( * ) Notice: Subject to any disclaimer, the term of this patent is extended or adjusted under 35 U.S.C. 154(b) by 1032 days.

(21) Appl. No.: 17/775,466

(22) PCT Filed: Nov. 6, 2020

(86) PCT No.: PCT/EP2020/081370
§ 371 (c)(1),
(2) Date: May 9, 2022

(87) PCT Pub. No.: WO2021/089834
PCT Pub. Date: May 14, 2021

(65) Prior Publication Data
US 2022/0373557 A1 Nov. 24, 2022

(30) Foreign Application Priority Data

Nov. 8, 2019 (EP) ..................................... 19208187
Sep. 23, 2020 (EP) ..................................... 20197910

(51) Int. Cl.
*G01N 33/68* (2006.01)
*G01N 15/02* (2024.01)
(Continued)

(52) U.S. Cl.
CPC ..... *G01N 33/6803* (2013.01); *G01N 15/0211* (2013.01); *G01N 21/6486* (2013.01);
(Continued)

(58) Field of Classification Search
CPC ............... G01N 33/68; G01N 33/6803; G01N 15/0211; G01N 15/01; G01N 21/64;
(Continued)

(56) References Cited

U.S. PATENT DOCUMENTS 5,328,822 A 7/1994 McKinney et al.
5,487,870 A 1/1996 McKinney et al.
(Continued)

FOREIGN PATENT DOCUMENTS

AU 2004252258 A1 1/2005
CN 108139309 A 6/2018
(Continued)

OTHER PUBLICATIONS

Copy and Translation of Korean Office Action for Korean Patent Application No. 10-2022-7019318 dated Jan. 11, 2025, 16 pages.
(Continued)

*Primary Examiner* — Maureen Wallenhorst
(74) *Attorney, Agent, or Firm* — Westman, Champlin & Kochler, P.A.

(57) ABSTRACT

A method for measuring characteristics of particles in solution and to a device for performing the same, wherein the method includes the steps of providing a vessel containing a sample of the particles in solution, wherein the sample has preferably a volume between 0.1 μL and 15 μL, providing a monochromatic light source and a light detector, transmitting light from the monochromatic light source to the vessel containing the sample, detecting light emitted from the vessel with the light detector, and determining characteristics of the particles in solution in the sample based on a dynamic light scattering (DLS) measurement.

35 Claims, 23 Drawing Sheets

(51) Int. Cl.

| | |
|---|---|
| *G01N 15/0205* | (2024.01) |
| *G01N 21/64* | (2006.01) |
| *G01N 15/00* | (2006.01) |
| *G01N 15/01* | (2024.01) |

(52) U.S. Cl.

CPC ............... *G01N 2015/0038* (2013.01); *G01N 2015/0092* (2013.01); *G01N 15/01* (2024.01); *G01N 2015/0222* (2013.01)

(58) Field of Classification Search

CPC ............... G01N 21/6486; G01N 21/51; G01N 2015/0038; G01N 2015/0092; G01N 2015/0222; G01N 2015/019; G01N 2021/0346

USPC .... 436/86, 164, 165, 172; 422/82.05, 82.08, 422/82.09

See application file for complete search history.

(56) References Cited

U.S. PATENT DOCUMENTS

| | | | |
|---|---|---|---|
| 5,575,977 A | | 11/1996 | McKinney et al. |
| 5,973,779 A | | 10/1999 | Ansari et al. |
| 7,330,243 B2 | | 2/2008 | Betzel et al. |
| 10,073,034 B2 | | 9/2018 | Widzgowski |
| 10,317,327 B2 | | 6/2019 | Corbett |
| 10,618,051 B2 | | 4/2020 | Baaske et al. |
| 2002/0066867 A1 | * | 6/2002 | Ross, III ............ G01N 21/9508 250/341.1 |
| 2004/0072356 A1 | | 4/2004 | Senisterra et al. |
| 2005/0172887 A1 | | 8/2005 | Betzel et al. |
| 2006/0203859 A1 | * | 9/2006 | Cable ..................... H01S 5/141 372/20 |
| 2010/0136611 A1 | | 6/2010 | Maurer |
| 2012/0281215 A1 | | 11/2012 | Peters |
| 2013/0119276 A1 | | 5/2013 | Widzgowski |

| | | | |
|---|---|---|---|
| 2014/0330459 A1 | * | 11/2014 | Baumgardner ......... G01S 17/95 701/14 |
| 2017/0361326 A1 | * | 12/2017 | Baaske ................... B01L 9/065 |
| 2018/0259535 A1 | | 9/2018 | Verdine et al. |
| 2018/0284002 A1 | | 10/2018 | Baaske et al. |
| 2018/0313758 A1 | | 11/2018 | Hsieh et al. |
| 2019/0086316 A1 | * | 3/2019 | Rice ..................... A61B 5/0075 |
| 2022/0404284 A1 | * | 12/2022 | Baaske ............. G01N 21/6486 |

FOREIGN PATENT DOCUMENTS

| | | | |
|---|---|---|---|
| EP | 3159674 A1 | | 4/2017 |
| FR | 2856792 A1 | | 12/2004 |
| JP | H05506928 A | | 10/1993 |
| JP | 2005221503 A | | 8/2005 |
| JP | 2007516411 A | | 6/2007 |
| JP | 2013104876 A | | 5/2013 |
| JP | 2018-507387 A | | 3/2018 |
| WO | 9116450 A1 | | 10/1991 |
| WO | 2005001449 A1 | | 1/2005 |
| WO | 2019/166650 A1 | | 9/2019 |
| WO | 2019/201894 A1 | | 10/2019 |

OTHER PUBLICATIONS

Translation of Chinese Office Action for Chinese Patent Application No. 202080092390.3, dated Jan. 23, 2025, 32 pages.

Office Action for European Patent Application No. 20 800 668.4, dated Dec. 13, 2023, 6 pages.

Canadian Office Action for Canadian Patent No. 3,153,480, dated Aug. 14, 2024, 5 pages.

Japanese Office Action for Japanese Patent Application No. 2022-525259, dispatched Nov. 2, 2023, 12 pages.

International Search Report and Written Opinion for International Application No. PCT/EP2020/081370, date of mailing Jan. 28, 2021, 20 pages.

Japanese Notice of Reasons for Rejection, for Japanese Patent Application No. 2022-525257, dated Jun. 20, 2024, 6 pages.

\* cited by examiner

CHARACTERIZATION OF PARTICLES IN SOLUTION

CROSS-REFERENCE TO RELATED APPLICATION

This Application is a Section 371 National Stage Application of International Application No. PCT/EP2020/081370, filed 6 Nov. 2020 and published as WO 2021/089834 A1, on 14 May 2021, in German, which claims priority to EP 19208187.5, filed on 8 Nov. 2019, and EP 20197910.1, filed on 23 Sep. 2020, the contents of which are hereby incorporated by reference in their entireties.

FIELD OF INVENTION

In general, the present invention relates to a method to characterize particles in a solution on the basis of dynamic light scattering. In particular, the present invention relates to a method which allows characterization of the three-dimensional structure of proteins and the change of the three-dimensional structure of proteins in a solution, preferably including their stability for example in dependence of temperature, especially in case of small sample volumes using dynamic light scattering (DLS), preferably measured for less than 1 sec, for example in combination with differential scanning fluorimetry (DSF); and to a device for performing the same. The present invention preferably provides a method and a system which provide enhanced accurate measurements of aggregation and intrinsic properties, for example folding of a particle, e.g., a protein, within a short time and a single system.

BACKGROUND

Determining characteristics of products in a fast and accurate manner is crucial for many applications. For example, in pharmaceutical or biotechnological contexts as well as in food industry and material science, it is important to ensure a high degree of purity and/or a stable quality of a product during its production and potential storage. Quality controls are routinely performed based on a sample of the product and/or a sample comprising the product such as particles, e.g. proteins, in solution. These controls are typically time consuming and can cause a considerable delay until results are available. Hence, for reducing costs arising from impurities and/or undesired product properties, it would be desirable to have at hand solutions for assessing characteristics of a product, e.g. of particles in solution, with high accuracy and preferably in real-time.

One example of such particles are proteins. Proteins are involved in almost all cellular processes and thus, crucial for the function of cellular organisms including humans. Depending on their function, proteins can be classified for example as structural proteins determining the structure of cells and tissues; proteins with catalytic functions, i.e. enzymes; ion channels regulating cellular ion concentrations and thus osmotic homeostasis and signal transduction; transport proteins; regulatory proteins including hormones; and proteins involved in immune reactions such as antibodies. The amount and/or activity of a protein can be affected for example in case of exposure to physiological stress conditions including high temperatures and/or in case of hereditary diseases. Due to their prevalence and their impact on cellular processes, changes in the amount and/or activity of a protein can have a significant impact on an organism's survival and health.

Due to their relevance, proteins have been intensively investigated in view of their structure, function, distribution, level, and potential use in various applications including medicine. Proteins are macromolecular compounds consisting of amino acids that are linked by peptide bonds. The specific amino acid sequence, also referred to as the primary structure of a protein, is genetically determined. The amino acid sequence can be folded because of hydrogen bonds between amino acids residues of a protein, which results in a conformation that is also referred to as secondary structure, wherein the spatial arrangement of the amino acid sequence is referred to as tertiary structure. The tertiary structure, and thus the three-dimensional folding of a protein, is of special interest as its investigation provides not only information about the molecular structure of a protein. It can further provide detailed information about the spatial arrangement of reactive amino acid residues, e.g. in the catalytically active center of enzymes or in the antigen binding site of antibodies, and thus, about its activity. Furthermore, some proteins have a quaternary structure, which refers to an aggregation and/or association of proteins thus forming a stable (oligo)protein with the individual proteins being referred to as subunits of the (oligomeric) protein. As a deviation of a protein's native conformation(s) is usually associated with a reduction in its efficacy, especially the three-dimensional structure of a protein can be considered as being essential for its biological effect.

Optimizing the availability of a protein, especially in a biologically active conformation, represents a promising approach in therapeutic contexts for example. In case a subject exhibits a reduced level of a protein compared to the level that can be observed in other subjects such as a control group, it can be beneficial for the subject to obtain a predetermined amount of said protein. Especially for therapeutic applications, a high degree of purity of the protein of interest in a given conformation is required to avoid undesired immune reactions upon administration. For the same reason, active substances such as active ingredients of protein-based biopharmaceuticals have to be stable during storage, i.e. the proteins of interest comprised in a biopharmaceutical shall remain intact and in the intended conformation and thus, shall not degrade, change their three-dimensional structure and/or form aggregates during storage.

Since active substances, such as antibodies, have been developed in such a way that they are only active in their native form, denatured active substances are often not effective and must be avoided. Denaturation refers to a structural change in biomolecules, such as proteins, which in most cases involves the loss of the biological function of these molecules. Denaturation can be due to either physical or chemical influences. Denaturation of particles, such as antibodies, should be avoided because it reduces efficacy. Thus, active ingredient formulations have to be developed such that a denaturation of the drugs can be prevented, i.e. stabilize them thermally, chemically and/or temporally. Moreover, also aggregation or aggregation of active substances can also lead to ineffectiveness. In addition, aggregated and/or denatured particles, for example administered aggregated antibodies, can trigger a reaction of the immune system in the body and must therefore be avoided in drugs or their proportion in the drug should be minimized. Thus, aggregation of particles, e.g. in antibody therapeutics, should be avoided as it causes a reaction of the immune system and can also lead to a reduction of efficacy.

However, it is often not clear why a particle aggregates and/or denatures: Does a particle aggregate because it denatures, i.e. is not present in its native form, or does it aggregate in its native form and then denature?

Different approaches have been developed aiming at characterizing the three-dimensional structure of (oligomeric) proteins under various environmental conditions, including native and chemical and/or thermal denaturation conditions. Investigating the stability of the three-dimensional folding of a protein in dependence for example of temperature, pH, and/or presence of other chemical components, can be highly advantageous for optimizing storage conditions, for example of protein-based biopharmaceuticals. For determining the stability of a protein differential scanning fluorimetry (DSF) methods can be applied for example including nano-DSF. The presence of larger particles such as undesired protein aggregates can be analyzed for example using qualitative methods including back reflection, whereas size distributions of proteins in a solution can be investigated using for example dynamic light scattering (DLS) based analyses.

For a comprehensive characterization of particles, it is often not sufficient to analyze only the aggregation or only the denaturation separately. However, existing systems are not able to measure aggregation and (un)folding of proteins simultaneously with high sensitivity, although the interaction of both parameters is in most cases of interest as well. For example, the Prometheus™ device (Nanotemper) can measure both aggregation and (un)folding of a protein in solution, but in case of aggregation the sensitivity is limited so that the presence of some small aggregates cannot be distinguished from the presence of few large aggregates. The latter could for example be achieved by combining the device with another device such as a DynaPro® plate reader (Wyatt Technology). However, when using the latter additionally technical limitations including a lower heating rate results in a loss of information whether unfolding or aggregation occurred first upon exposure of the particle to heat.

Hence, there is still a need to have at hand alternative solutions for comprehensively and efficiently characterizing a particle like a protein in solution in high throughput ensuring reproducible, quantitative results even in cases where there is a low abundance of particles.

SUMMARY

The present invention is, inter alia, based on the finding that the three-dimensional structure of particles in solution can be analyzed with high sensitivity and reproducibility in high throughput by performing a DLS measurement, preferably in combination with a nano-DSF measurement based on the same sample comprising said particles in solution, even in case of a small sample volume in a short time. Based on said measurements, aggregation and free energy of folding of a protein can be determined in a fast and accurate way, preferably within a single device. Moreover, quality controls can be massively accelerated as information on the presence or absence of particle aggregates in solution and/or a deviation of an expected particle size distribution can be obtained, e.g., in two seconds or even less for approximately 48 samples using the method and the system of the present invention. For comparison, existing approaches using DLS require at least about 12 second for one sample. Thus, even real-time, e.g. liquid flow, measurements can be performed for characterizing particles in solution using the method and the device of the present invention.

In particular, with the system and method according to the present invention both, "intra-particle" processes and "inter-particle" processes can be measured, e.g. the denaturation and the aggregation of particles in solution can be measured and, moreover, even quasi simultaneously (i.e. essentially simultaneously) or simultaneously.

For instance, "intra-particle" processes are preferably related to folding/unfolding and in general to the 3D structure of the particle (primary, secondary, tertiary, quaternary structure) The denaturation of the particles is also an "intra-particle" process and can be measured in the procedure and system according to the present invention by measuring the intrinsic particles fluorescence (e.g. tryptophan fluorescence, tyrosine fluorescence). At the same time, particle aggregation, an "inter-particle" process that changes particle size, can be measured by scattering unabsorbed light.

It is beneficial to measure the thermally induced denaturation and aggregation of particles/molecules simultaneously, for example, to determine if the denaturation of the particle is induced by aggregation or if the aggregation of the particles is induced by the denaturation. In other words: it is beneficial to understand if the particles aggregate in their native conformation or if they aggregate in their unfolded or partially unfolded conformation. This knowledge allows for a better understanding of the aggregation mechanism and will thus improve the development process of a stable formulation (e.g. comprising a buffer with stabilizing ingredients) of a particle under study. As the aforementioned processes may happen at a different time scale (e.g. about 1 sec to several hours) and in a different order it is especially beneficial to measure nano-DSF and DLS simultaneously over time to monitor the kinetics of these interdependent processes.

The present invention is defined by the features of the independent claims. Preferred embodiments of the present invention are defined by the dependent claims.

The present invention relates to a method to measure characteristics of particles in solution, said method comprising the step of providing a vessel comprising a sample of said particles in solution. The sample has preferably a small volume, e.g. between 0.1 µL and 15 µL. The method comprises preferably the steps of providing a light source which emits substantially monochromatic light, providing a light detector and transmitting light from the monochromatic light source to the vessel comprising the sample. In other words, the particles in the vessel are irradiated with light from the light source, wherein scattered light from the particles is detected with the light detector. Still in other words, light coming from the vessel, i.e., light which is quasi emitted from the vessel is detected with the light detector, wherein characteristics of said particles in solution comprised in the sample can be determined based on a dynamic light scattering (DLS) measurement. Herein, light emitted/coming from the vessel is also referred to as "emitted light" and used interchangeable with the term "scattered light" or "backscattered light" from the sample after it has interacted with the sample.

Preferably, the sample has a volume between 0.1 µL and 15 µL, more preferably between 1 µl and 15 µl, even more preferably between 8 µL and 12 µL. The sample is preferably provided in a vessel with a small volume, e.g., in a well of a multiwell plate or in a capillary, which provides the further advantage that the capillary can be easily filled by means of capillary forces. For instance, a single capillary or even a plurality of capillaries mounted on an array (holder) can be immersed into the solution with the sample, such that each capillary can completely soak itself within a few seconds due to the capillary forces.

Preferably, the light from the monochromatic light source is coherent and has preferably a wavelength between 350 nm and 500 nm, preferably of 405 nm, 445 nm, or 488 nm. A person skilled in the art understands that a real light sources can of course never be exactly monochromatic, i.e., have a zero optical bandwidth. Hence, the term monochromatic light source refers to a light source with a very limiting wavelength range or bandwidth, as mentioned above. In other words, the term monochromatic and quasi-monochromatic are used interchangeable within the present application. For instance, laser sources are often monochromatic or quasi-monochromatic, i.e., the optical bandwidth is small enough that certain behavior of the light can hardly be distinguished from that of truly monochromatic light.

Preferably, the (quasi-)monochromatic light source is a coherent light source, e.g., a laser, preferably a diode laser, preferably a diode laser selected from the group consisting of frequency stabilized diode laser, DPSS laser, PPLN frequency doubled diode laser, frequency multiplied DPSS laser, diode pumped fiber laser, frequency multiplied diode pumped fiber laser, and diode pumped upconversion fiber laser. Preferably, the laser has a coherence length of at least 0.1 mm. The laser has preferably a coherence length of at least 0.1 mm, preferably at least 1 mm.

Preferably, the laser has a power between 1 mW and 200 mW, preferably between 10 mW and 100 mW, more preferably between 45 mW and 80 mW, even more preferably between 50 mW and 70 mW. The laser may also have a power between 1 mW and 200 mW, preferably between 10 mW and 180 mW, more preferably between 50 mW and 150 mW, even more preferably between 70 mW and 120 mW, for example at 100 mW. Preferably, a DLS laser with an electronically/digital changeable/controllable output can be used.

Preferably, the monochromatic light is delivered from the monochromatic light source to the vessel/sample via a laser wavelength single mode fiber. Preferably, a polarization maintaining (PM) fiber is used, e.g., a laser wavelength polarization maintaining single mode fiber. According to a further embodiment it may be advantageous to use a fiber which does not maintain the polarization. It is further preferred to focus the light subsequently, e.g., by means of an objective lens, on a focal spot within the vessel.

Preferably, light from the monochromatic light source is transmitted to the vessel with an angle $\varphi_L$ to a longitudinal axis of the vessel, wherein $\varphi_L$ is preferably between 0 degrees and 45 degrees, preferably with a focal point within the vessel. Preferably, light detected with the light detector is emitted (or scattered, backscattered) from the vessel with an angle $\varphi_D$ to a longitudinal axis of the vessel, wherein $\varphi_D$ is between 0 degrees and 45 degrees, wherein the value of $\varphi_L$ is preferably identical to the value of $\varphi_D$. Preferably, an angle cps between the light that is transmitted from the monochromatic light source to the vessel and the light emitted from the vessel that is detected with the light detector is between 0 degrees and 150 degrees, preferably between 10 degrees and 150 degrees, more preferably between 10 degrees and 60 degrees. The above-mentioned angles of the emitted or scattered light are preferably measured with regard to the vessel, since the position of the vessel can be determined within the device. A person skilled in the art understands, however, that the light scattered or emitted from the particles within the vessel is the light which contains the information of the particles, which can be used for their characterization. For instance, the method of the present invention can be used to perform a DLS measurement, which is based on the light scattered from the particles in the solution. Moreover, the method of the present invention can also be used to perform a DSF measurement which is based on fluorescence light emitted from the particles. Macroscopically, the scattered light and the fluorescence light is coming/emitted from the vessel.

Preferably, the transmitted monochromatic light is focused in the vessel comprising the sample using an objective lens, wherein the light emitted from the vessel is preferably also focused by said objective lens. The objective lens has preferably a focal length between 10 mm and 200 mm. Preferably, the transmitted monochromatic light is focused in the vessel with a focal spot having a full width at half maximum (FWHM) between 3 μm and 30 μm, preferably resulting in a measurement volume between 0.01 nl and 0.1 nl, preferably between 0.01 nl and 0.02 nl, more preferably about 0.016 nl.

Preferably, the light detector is a photomultiplier tube (PMT), a silicon photomultiplier (SiPM), or an Avalanche photodiode (APD) photon counting detector, more preferably a PMT or a SiPM.

Preferably, the DLS measurement is obtained in less than 5 sec, preferably in less than 1 sec, preferably in between 200 ms to 800 ms, more preferably in about 500 ms.

Preferably, the DLS measurement is performed only once per sample at a specific temperature, e.g. to enhance speed of the measurement. The DLS measurement can, however, be performed multiple times per sample/vessel at the same temperature and/or at different temperatures, e.g., to calculate a means of the measurement (e.g. at the same temperature) and/or to take into account different conditions of the particles (e.g. at different temperatures).

Preferably, the DLS measurement comprises the step of performing at least one correlation operation, preferably at least one autocorrelation operation.

Preferably, the DLS measurement comprises the steps of obtaining an analog output signal obtained from the light detector; and processing the obtained analog output signal. Preferably, the step of processing the obtained analog output signal comprises the step of digitalizing the obtained analog output signal into a digitalized output signal. Digitizing the (entire) analog output signal from the detector provides certain advantages over the prior art which will be discussed in further detail below. In particular, the resulting digitalized output data may be considered as a digitalized raw signal, which is, however, easier to handle subsequently depending on the intensity of the light detected by the detector. In short, the digitalized output data can be subsequently processed with analog process means or processed as by digital process means, e.g., to discriminate individual peaks for individual photons.

Hence, the step of processing the output signal further comprises the step(s) of i) processing the digitalized output signal as a digitalized single photon pulse signal, preferably in case the intensity of the detected light emitted from the vessel is below 2 million detected photons per second; and/or ii) processing the digitalized output signal as discrete values of an analog signal, preferably in case the intensity of the detected light is above 2 million detected photons per second. Preferably, the step of processing the obtained output signal comprises either step i) or step ii), and wherein the time to decide whether to process the digitalized output signal as a digitalized signal according to step i) is less than 1 sec, preferably maximal 0.05 sec, preferably by using an FPGA (Field Programmable Gate Array). Moreover, both signals, i.e., photon counting signal and discrete value signal, may be processed simultaneously. Like this, the decision whether to process according to step i) or ii) can be met after the measurement.

Preferably, the step of processing the obtained output signal further comprises the step(s) of storing the processed digitalized output signal obtained from step i) or step ii); or storing the processed digitalized output signals obtained from step i) and step ii); and further processing one of the stored output signals.

As an example how the signal is processed, if it is processed as a photon counting signal and/or an analog signal, is not pre-determined by the detector detecting the photon, for example as it would be when using a dedicated photon-counting detector, but at a later stage by algorithms in for example a FPGA (Field Programmable Gate Array), ASIC (application-specific integrated circuit) or other programmable means. Preferably these algorithms can be changed, for example improved, without changing the hardware. For example a limit of 2 Million photons at which the algorithm changes from flagging the signal as photon counting signal to flagging it as analog signal, can be updated and/or changed by firmware and/or software means. For example the limit can be switched from 2 Million detected photons per second to for example 1 Million detected photons per second or 4 Million detected photons per second. This is preferable with respect to existing solutions in which the hardware, for example the photon counter, has to be exchanged to alter the above mentioned limit.

Preferably, the method comprises further the step of measuring fluorescence. The measured fluorescence is preferably the fluorescence of said particles in solution comprised in the sample and/or the fluorescence of the material of the vessel itself, wherein said fluorescence is preferably an autofluorescence of said particles/the vessel material. Preferably, the method comprises further the step of determining the position of the vessel based on the measured fluorescence, and optionally repositioning the vessel relative to the light source, i.e., repositioning the vessel and/or the light source, based on the measured fluorescence and the determined vessel position. The step of determining the position of the vessel preferably also works for samples without (auto)fluorescent particles by using vessels which show enough autofluorescence themselves. In other words, the method of the present invention preferably determines the position of the vessel, e.g., a capillary, by a fluorescent measurement, wherein the detected fluorescence may be based on the particles and/or the material of the vessels. For instance, vessels formed from glass or quartz glass already produce enough autofluorescent radiation for determining the position of the vessel based on the mentioned fluorescence measurement, even in cases where no sample or a sample without (auto)fluorescence particles is present in the vessel.

Alternatively or additionally, the method according to the present invention preferably comprises a further step of measuring back-reflection of the vessel comprising the sample which can be used for characterization of the particles of the sample and/or can be used for determining the position of the vessel.

Preferably, the method comprises further the step of tempering the vessel over time at least with a first temperature at a first time point and a second different temperature at a second time point. Thus, in case the characteristics of particles are determined at two different temperatures, it is possible to measure the change of characteristics. Accordingly, the method of the present invention can measure the change in characteristics of particles in solution by conducting the method of the present invention by a first temperature T1 and then by conducting the method by a second different temperature T2 or a multitude of different temperatures Txy and determine the change in the characteristics of the particles by comparing T1 with T2 or the multidute of temperatures Txy.

Preferably, the present invention relates to a method to measure characteristics of particles in a solution with the steps of:

(a) providing a sample comprising the particles in a solution;

(b) providing a temperature control system for creating a defined temperature of said sample probe by contact heating and/or cooling;

(c) measuring the particles at a first temperature;

(d) creating a $2^{nd}$ temperature within the sample by means of the temperature control system;

(e) measuring the particles in the sample at this $2^{nd}$ temperature, and (f) characterizing the particles based on said two measurements.

According to the present invention, the measuring steps c) and e) are the presently disclosed DLS measuring steps and/or the presently disclosed nano DSF measuring steps. According to a preferred embodiment, both measuring steps c) and e) comprise the DLS measuring steps, an additional first fluorescence readout and a second fluorescence readout.

Preferably, the step of tempering the vessel over time at least with a first temperature at a first time point and a second temperature at a second time point comprises tempering the vessel with a tempering rate between 0.01° C. per minute and 30° C. per minute, preferably between 0.1° C. per minute and 10° C. per minute, and/or wherein the first temperature and the second temperature are between −20° C. and 160° C.

Preferably, a specific temperature, preferably in the above mentioned range and maintaining said temperature for a specific time, e.g., more than 10s, more than 1 minute or even longer, e.g., a isothermal mode, with a specific accuracy preferably between +/−0.01° C. and +/−1.5° C., preferably between +/−0.01° C. and +/−0.5° C. provides certain advantages of the measurement regarding homogeneity, reproducibility and precision:

Preferably, the method comprises further the step(s) of performing a nano differential scanning fluorimetry (nano-DSF) measurement; and/or measuring back-reflection of the vessel comprising the sample.

Preferably, the method comprises further the steps of providing a further light detector, and measuring static scattering light of the vessel comprising the sample using the further light detector, preferably with an angle φ to a longitudinal axis of the vessel, wherein φ is preferably between 10 degrees and 150 degrees, more preferably between 10 degrees and 60 degrees.

Preferably, the vessel for accommodating the small sample volume is small vessel such as a capillary and/or multi-well plate. Preferably, the capillary is a capillary tube sample vessel or just capillary tube or capillary. A capillary tube of the present invention comprises preferably a substantially constant inner diameter and/or a substantially constant outer diameter over the entire length of the capillary. Preferably, the capillaries are made of glass, preferably glass with no or only minor auto fluorescence characteristics, for example of borosilicate glass and/or quartz glass and/or synthetic fused silica.

Said capillary has preferably a round cross-section and preferably an inner diameter between 0.1 mm and 1 mm, preferably between 0.15 mm and 0.5 mm, and preferably an outer diameter between 0.2 mm and 1.2 mm, preferably between 0.65 mm and 1 mm and a length between 5 mm and 70 mm, preferably between 32 mm and 50 mm, more preferably of about 50 mm. Based on said diameters it is further preferred to choose a compromise between the thickness of the wall of the capillary to be large enough and therefore be stable to be handled manually and thin enough to minimize optical refraction within a desired range. The preferred thickness of the capillary wall may therefore be chosen depending on the individual requirements, e.g. manual handling, automatic handling etc.

Moreover, depending on the application, shorter or longer capillaries may be advantageous. The effects based on the length of the capillaries are chosen preferably depending on the desired application. Very short capillaries for example have the advantage that they have only a very small volume, which is advantageous with respect to the little amount of material needed (efficiency). Very short capillaries may advantageously be filled completely by means of capillary forces (when they have a correspondingly adapted diameter). If they are short enough, the capillaries do not even have to be tilted with respect to gravitation (g) since capillary forces themselves completely fill the capillary antiparallel to g. Short capillaries also have an advantage regarding space; thus, more capillaries can be placed in a limited surface.

Longer capillaries provide the advantage that a sealing of one or both ends is not necessary, e.g., the effect of evaporation of the solution is small in relation to the measurement time according to the present invention. For instance, capillaries with a length longer than 32 mm provide a low evaporation rate within the preferred duration of the measurements of the present invention.

Preferably, a plurality of vessels is provided, wherein each vessel comprises a sample of particles in solution, and wherein characteristics of particles in solution are measured for each vessel according to the method of the present invention. Preferably, a fluorescence measurement for each vessel is followed by a DLS measurement for each vessel; or a DLS measurement for each vessel is followed by a fluorescence measurement for each vessel; or a fluorescence measurement and a DLS measurement is performed for one vessel of the plurality of vessels followed by a fluorescence measurement and a DLS measurement for another vessel of the plurality of vessels. More preferably, a fluorescence measurement is simultaneously performed with a DLS measurement for each vessel of the plurality of vessels.

Preferably, the characteristics are selected from the group consisting of particle size distribution, aggregation temperature, melting temperature, transition temperature, unfolding temperature onset, temperature of liquid-liquid phase separation ($T_{LLPS}$), change in the free fenergy of unfolding, second virial coefficient ($B_{22}/A_2$), self-interactions of particles, colloidal stability, hydrodynamic radius, repulsive or attractive interaction between particles (kD), solubility, long-term protein stability and critical denaturant concentrations.

For instance, determining the size increase onset (from the radius over temperature measurement) characteristics regarding unfolding/oligomerization/aggregation are derivable in contrast to onset of aggregation.

The activation energy of unfolding may be derivable, e.g., from subsequent experiments with different heating rates and may be an application to assess colloidal stability.

The present invention relates further to a device for measuring characteristics of particles in solution, preferably in accordance with the method of the present invention, wherein said device comprises means for accommodating at least one vessel comprising a sample of said particles in solution, preferably for accommodating between 0.1 to 15 µL of said particles; a monochromatic light source and a light detector; means for performing a DLS measurement; and control means adapted for controlling the means for accommodating at least one vessel, controlling the monochromatic light source for transmitting light from the monochromatic light source to the at least one vessel, controlling the light detector for detecting signals from the at least one vessel, and controlling said means for performing a DLS measurement.

Preferably, said device further comprises means for performing a correlation operation, preferably an autocorrelation operation, wherein said autocorrelation operation is preferably an autocorrelation logic embodied in hardware and/or software.

Preferably, said device further comprises means for digitalizing signals obtained from the light detector, wherein said means preferably comprises a field programmable gate array (FPGA), wherein the control means are preferably further adapted for controlling said means for digitalizing signals obtained from the light detector.

Preferably, said device further comprises means for measuring the fluorescence of said particles in solution comprised in the sample, wherein the control means are further adapted for controlling said means for measuring the fluorescence of said particles in solution comprised in the sample.

Preferably, said device further comprises positioning means for positioning the means for accommodating the sample of said particles in solution, wherein the control means are further adapted for controlling the positioning means for accommodating the sample.

Preferably, said device further comprises a temperature control system for tempering the vessel over time at least with a first temperature at a first time point and a second temperature at a second time point, wherein the control means are further adapted for controlling said temperature control system for tempering the vessel over time at least with a first temperature at a first time point and a second temperature at a second time point.

Preferably, said device further comprises means for performing a nano-DSF measurement and/or means for measuring back-reflection, wherein the control means are further adapted for controlling said means for performing a nano-DSF measurement and/or said means for measuring back-reflection.

Preferably, said device further comprises a further light detector; and means for performing a static scattering light measurement, wherein the control means are further adapted for controlling said means for performing a static scattering light measurement.

Preferably, said device further comprises a single mode fiber; and means for delivering monochromatic light from the monochromatic light source via said single mode fiber, wherein the control means are further adapted for controlling said means for delivering monochromatic light from the monochromatic light source via said single mode fiber.

BRIEF DESCRIPTION OF THE DRAWINGS

In the following, preferred embodiments of the present invention are described in detail with respect to the Figures. The Figures show.

DETAILED DESCRIPTION

Figure 1A:
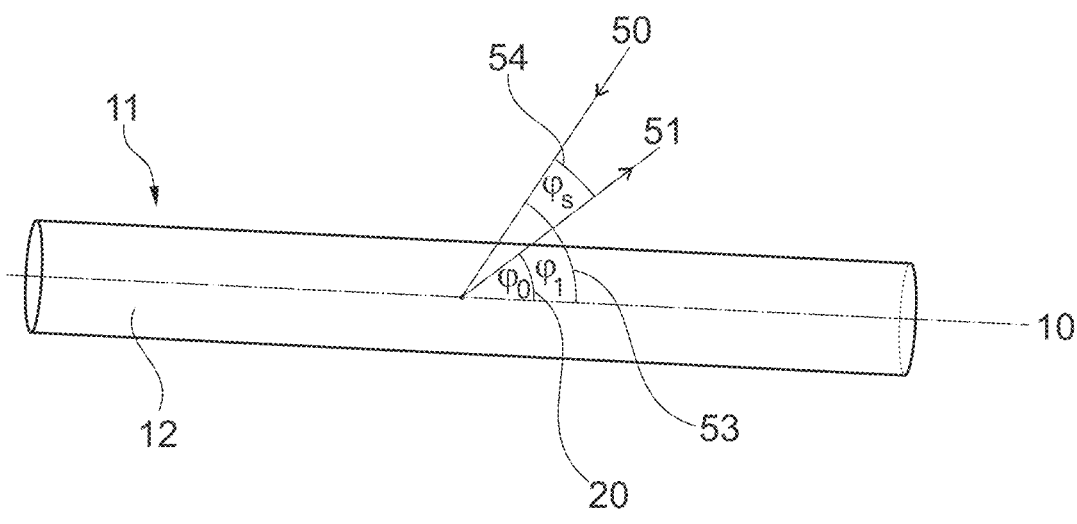
FIG. 1: A) Angle of main light beams to capillary axis. B) A DLS optics is positioned obliquely to the capillary axis to avoid detection of reflections.

In the following, general principles of the present invention will be discussed in further detail and discussed on the basis of illustrative examples or preferred embodiments of the present invention.

In particular, the present invention relates in a first aspect to a method to measure characteristics of particles in solution, said method comprising the steps of providing a vessel comprising a sample of said particles in solution, wherein the sample has preferably a volume between 0.1 μL and 15 μL; providing a monochromatic light source and a light detector; transmitting light from the monochromatic light source to the vessel comprising the sample; detecting light emitted from the vessel with the light detector; and determining characteristics of said particles in solution comprised in the sample based on a dynamic light scattering (DLS) measurement. The present invention provides the advantage that known DLS measurements are now performed in very small sample volumes, e.g., DLS measurement of a sample within a capillary which was never disclosed nor suggested by the prior art. Rather, the prior art teaches that DLS measurement requires volumes which are preferably larger than the above-mentioned sample probes. Moreover, the method of the present invention has the advantage that precise measurement results can be obtained with high throughput.

Preferably, the method further comprises a step of performing a nano-DSF measurement which has the advantage that based on DLS and nano-DSF measurements obtained by said method particle size distribution and potential particle aggregation can be assessed in a fast an accurate way, preferably within a single device. To increase precision of a measurement performed according to the method of the present invention, such as the DLS measurement and preferably also a nano-DSF measurement, said method preferably further comprises a step of measuring fluorescence to determine the position of the vessel. For instance, (auto) fluorescence of the particles in solution and/or autofluorescence of the vessel itself can be used, wherein by using the thus obtained fluorescence signal the position of the vessel can be determined. Thus, the position of the vessel comprising the sample with the particles in solution under study can be exactly determined and optionally (re-)positioning the vessel for optimizing accuracy of the respective measurement(s) is possible.

Hence, the method of the present invention is highly advantageous for measuring characteristics of particles in solution even in case of a small sample volume with high sensitivity using emitted monochromatic light, and thus scattered light, for a DLS measurement. Preferably, the method according to the present invention is performed automatically.

DLS is a method used for analyzing the diffusion coefficient of particles with a diffusion coefficient being a measure of the mobility of particles in a solution. In a DLS measurement, a sample in a vessel comprising particles in solution is irradiated with monochromatic light and the intensity of the scattered light is detected at a predetermined angle. The path length of the monochromatic light to a particle and the path length of the scattered light to the detector differ depending on the position of the respective particle within the vessel. By superimposing the light waves of the scattered light of different particles comprised in the sample, a sample specific interference pattern can be obtained based on the detected light. Consequently, the intensity of the detected signal depends on the positions of the particles within the vessel with their movement, i.e. Brownian molecular movement/motion, changing the length of the light path and thus, the obtained interference pattern. For example, the faster the particles move the faster the intensity of the signal changes resulting in a higher diffusion coefficient. Determining the diffusion coefficient of particles in solution comprised in a sample based on a DLS measurement is advantageous as it can be used for determining the hydrodynamic radius of the particles including their hydration shell, for example. Thus, by applying the method according to the present invention even small particles, such as particles with a hydrodynamic radius in the range from 0.1 nm to 3000 nm, preferably in a range from 0.5 nm to 1000 nm 2 to 3000 nm, can be detected and characterized with high sensitivity and accuracy.

Particles, the characteristics of which can be measured using the method according to the present invention, can be naturally occurring, biochemically and/or synthetically modified particles as well as synthetic particles or a combination thereof. Preferably, particles that have an average diameter of 1000 nm nm or less, preferably of 0.1 nm to 700 nm, more preferably of about 1 nm to 500 nm. Particles can be at least partially or completely biological particles (also referred to as bioparticles), and thus, the term "particle" used herein refers preferably not, e.g., to soot, gold particles or the like. The latter examples including gold particles are preferably neither comprised in the sample under study per se nor added thereto, e.g. in a sample processing and/or preparation step preceding the method according to the present invention. Their presence in the sample would not be advantageous as they scatter light relatively strong compared to bioparticles and thus, may mask scattered light signals from the (bio)particles under study. It is preferred that no so called "probe particles" are added to the sample as the sample is preferably studied in its native composition.

In the context of this invention, in particular the claims, it is noted that the terms "particle" or "particles" also relate to beads, particularly microbeads, vesicles, micelles, nanoparticles, or molecules, particularly biomolecules, e.g. nucleic acids (such as DNA, RNA, LNA, PNA), proteins, and other biopolymers and combinations thereof as well as biological cells (e.g. bacterial, prokaryotic or eukaryotic cells) or sub-cellular fragments, viral particles, virus like particles or viruses and cellular organelles and the like. Example for molecules are, but not limited to, fluorescent dyes, peptides, particularly polypeptides, saccharides, particularly polysaccharides, compounds, small molecules, fragments or surfactants The term "modified particle" or "modified bead" relates in particular to beads or particles which comprise or are linked to molecules, preferably biomolecules, or fluorescent dyes. This also comprises coating of such beads or particles with these (bio)molecules.

Further examples of particles according to the present invention are virus particles, virus-like particles, cells (especially cells with a diameter of less than 20000 nm), DNA molecules, RNA molecules, DNA-Origami, small molecules such as molecules having a molecular weight of less than 900 daltons, liposomes, proteins, protein complexes as for example in case of oligoproteins, and/or protein aggregates, wherein the type of particle, e.g. proteins comprised in the solution to be investigated, can be identical or different. Preferably, the particles in solution are identical types e.g. of proteins or complexes and/or aggregates formed thereof.

Preferably, the sample under study is directly obtained e.g. during or after the product production process. Thus, the sample is preferably not modified and/or amended before applying the method according to the present invention. If e.g. gold particles are added to a sample, the resulting effects would have to be considered when processing and/or interpreting the obtained results of the performed DLS, and preferably an additional fluorescence, measurement(s). Thus, investigating the particles under study in a directly obtained and not further amended sample is advantageous as information on characteristics of said particles in solution can be obtained without potentially time- and/or cost-consuming pre- and/or post-processing.

Herein, the terms "protein" and "oligoprotein" are used interchangeable if not specified specifically. In particular, the term "protein" as used herein encompasses any kind of amino acid sequence, i.e. chains of two or more amino acids which are each linked via peptide bonds. More specifically, the term "protein" used herein refers to any amino acid sequence of interest. Preferably, the amino acid sequence is at least 5 amino acids long, more preferably at least 10 amino acids, even more preferably at least 50, 100, 200 or 500 amino acids. Thus, the term "protein" covers short peptides such as oligopeptides, polypeptides, proteins, protein fragments, i.e. parts of known proteins, such as biologically active or antigenic parts including epitopes. As regards the function of the protein, there is no limitation.

Concentration range of the particles is preferably between a single particle, for example a nanoparticle, for a gold nanoparticle, to 500 mM, for example in case of a small molecule.

Figures 12, 13:
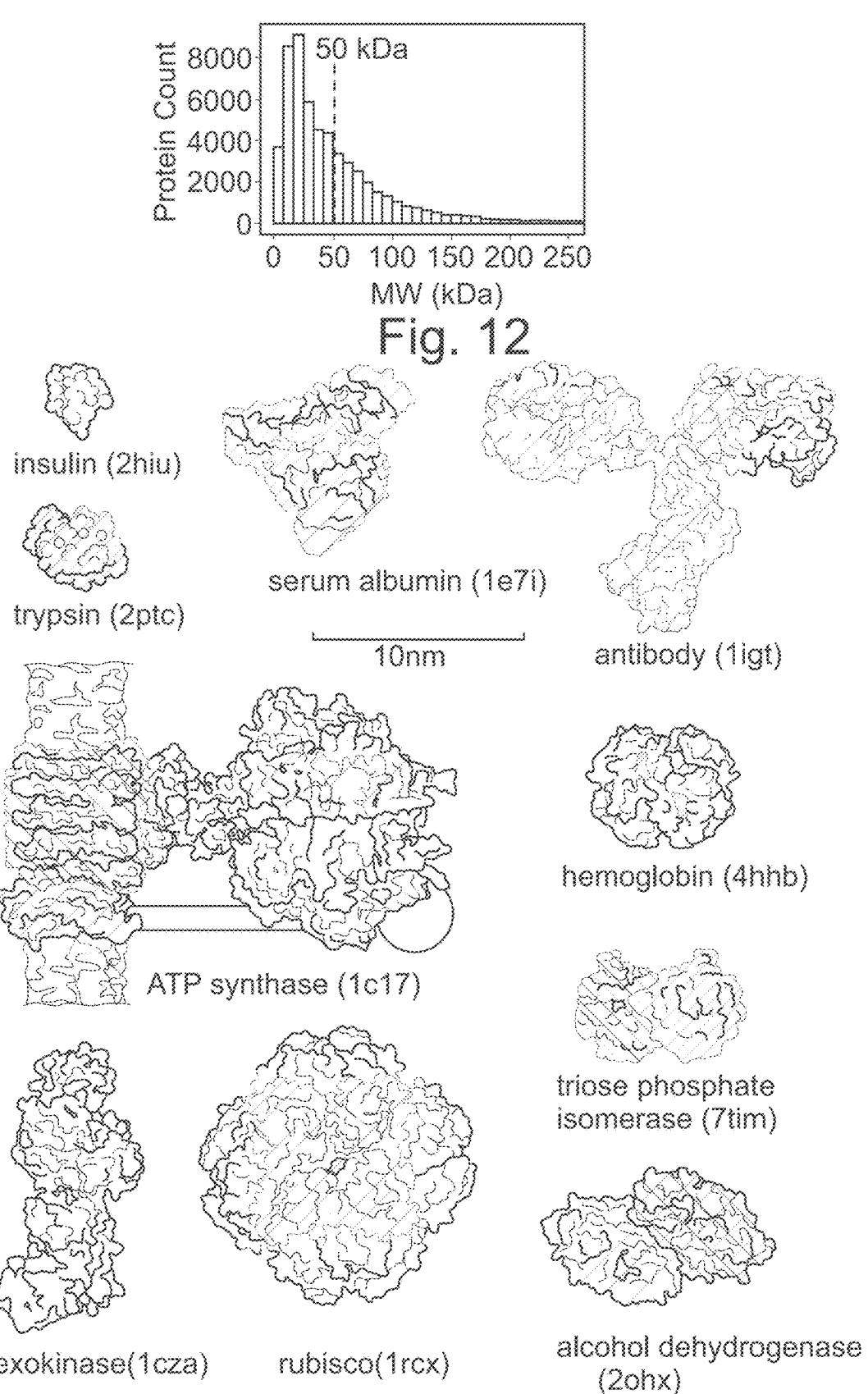
FIG. 12: Exemplarily protein molecular weight distribution (UniProt, human; https://smith.chem.wisc.edu/content/proteomics-technologies).
FIG. 13: Schemes of exemplarily proteins that can be characterized using the method and the device according to the present invention (http://book.bionumbers.org/how-big-is-the-average-protein/).

The particles in solution are preferably proteins in solution. As shown in Table 1 below ($R_{min}$ for proteins of different mass;

https://www.ncbi.nim.nih.gov/pmc/articies/PMC3055910/) and in FIG. 12, most proteins are e.g. smaller than 500 kDa Molecular Weight and therefore have a radius of less than 5 nm and/or a diameter of less than 10 nm. Thus, preferred proteins have a radius of less than 5 nm and/or a diameter of less than 10 nm. Furthermore, some preferred examples are shown in FIG. 13.

TABLE 1

| Protein M (kDa) | 5 | 10 | 20 | 50 | 100 | 200 | 500 |
|---|---|---|---|---|---|---|---|
| $R_{min}$ (nm) | 1.1 | 1.42 | 1.78 | 2.4 | 3.05 | 3.84 | 5.21 |

Examples for lower concentrations of proteins are 0.5 mg/ml for lysozyme, 0.4 mg/ml for insulin and 0.06 mg/ml for IgG. The preferred concentration range for proteins is 0.001 mg/ml to 250 mg/ml, more preferably from 0.01 mg/ml to 200 mg/ml.

Particles such as proteins can be particles that have been isolated from biological material, e.g. cell cultures used for in vitro protein production, and/or produced synthetically. The latter has several advantages as it is time and/or cost efficient and ensures a high degree of purity of the protein of interest. Preferably, the particles in solution are identical proteins or complexes and/or aggregates built thereof, wherein the proteins have been produced synthetically. Thus, highly accurate and sensitive measurements can be obtained for characterizing the particles in solution.

Several characteristics of particles in solution are of commercial and academic interest. For example, the size distribution of particles in solution is advantageous for assessing the particle composition in the solution including presence and/or amount of undesired particles such as degraded and/or aggregated proteins due to protein instability under specific conditions. As different particles may aggregate under different conditions, the aggregation condition for a given particle can be assessed that characterizes said particle, e.g. the temperature the particles can be exposed to with a given proportion, e.g. half, of the particles being aggregated. Hence, the aggregation temperature can be used to define the onset of aggregation ($T_{agg}$). The same rational can be applied in view of the temperature dependent folding and unfolding of particles via the particle-specific unfolding temperature onset. The melting temperature/point ($T_m$) is of further interest, which defines the temperature at which none of the potential folding states of a particle such as a protein is thermodynamically more favorable than another. Thus, said particles are present in either conformation, i.e. the natively folded conformation and an unfolded and thus, denatured conformation, in comparable amounts. The melting temperature can thus be used as an indicator of a particles' thermal stability. Furthermore, the free folding energy can be investigated which is directly related to protein stability and depends on the amino acid composition of a protein. The second virial coefficient ($B_{22}$, also referred to as $A_2$) refers to an indicator of the colloidal stability of a particle that can be further used for predicting protein aggregation with positive values referring to predominantly negative protein-protein colloidal interactions and negative values denoting net attractive protein-protein interactions (kD; diffusion interaction parameter).

Hence, the characteristics of particles in solution that can be measured using the method according to the present invention are preferably selected from the group consisting of particle size distribution, aggregation temperature, melting temperature, unfolding temperature onset, free folding energy, second virial coefficient ($B_{22}/A_2$), self-interactions of particles, colloidal stability, hydrodynamic radius, repulsive or attractive interaction between particles (kD) and critical denaturant concentrations.

Moreover, by determining the size increase onset (e.g. derivable from a radius over temperature measurement) characteristics regarding unfolding/oligomerization/aggregation are derivable in contrast to onset of aggregation. Additionally, the activation energy of unfolding may be derivable, e.g., from subsequent experiments with different heating rates, which is, e.g. a useful application to assess colloidal stability.

The method according to the present invention can be applied to measure characteristics of particles in solution, preferably an aqueous solution, by providing a vessel comprising a sample of said particles in solution, wherein the sample has preferably a volume between 0.1 µL and 15 µL.

Thus, a sample is analyzed which comprises some or all the particles in solution to be investigated, wherein said sample is comprised in a vessel. In case the vessel is for example a capillary, said sample has preferably a volume between 0.1 µL and 15 µL, preferably between 1 µl and 15 µl, and more preferably between 8 µL and 12 µL.

In case the vessel is for example a multi-well plate, said sample has preferably a volume between 5 µL and 40 µL in case the vessel is a 384 well plate, preferably between 50 µl and 200 µl in case the vessel is a 96 well plate, and preferably between 1 µL and 15 µL in case the vessel is a 1536 well plate. Such a small sample volume is advantageous when the available number of particles is limited and/or the particles under study are costly. Moreover, analyzing small sample volumes using the method according to the present invention has at least the following additional advantages: i) better masking of scattering on the vessel wall, i.e. the effect of light scattering on the vessel wall such as a capillary wall on the measurement can be minimized, ii) stronger scattering signals from the sample comprising the particles in solution under study and thus, reduced measurement times, iii) decreased probability of multiple scattering at high concentrations which is dependent on the number of particles in solution comprised in a sample, iv) less expensive monochromatic light sources, e.g. laser with shorter coherence length, can be used for obtaining measurements results of high quality and thus, accurate characterization of particles under study.

The sample comprising the particles in solution under study is comprised in a vessel, preferably a capillary or a well of a multi-well plate. In case of a capillary, said capillary can be made of a resin, plastic, a ceramic, a polymer or glass for example. Preferably, the capillary has open ends at both terminal ends in the longitudinal direction of the capillary. Preferably the capillary is a glass capillary. For accuracy and reproducibility of the method, according to the present invention, it is advantageous to reduce artefacts and signal noise which could affect the DLS measurement which is based on the light signal emitted from the vessel comprising a sample of the particles in solution. Hence, vessels made of glass are advantageous as glass affects light transmission and scattering less than other materials such as resins while being stable and inert even in case of high temperatures and extreme solution conditions e.g. acidic conditions. Hence, the capillary is preferably a glass capillary with a round cross-section and an inner diameter between 0.1 mm and 1 mm, preferably between 0.15 mm and 0.5 mm, and preferably an outer diameter between 0.2 mm and 1.2 mm, preferably between 0.65 mm and 1 mm, and a length between 5 mm and 70 mm, preferably between 32 mm and 50 mm, more preferably of about 50 mm. Preferably, the inner and/or outer diameter is constant over the entire length of the capillary, preferably both. Such a capillary is often called tube capillary to further emphasize the form of the capillary. The capillary wall acts like a lens and thus, has an optic effect. Hence, the thickness of the capillary wall can influence the precision and sensitivity of the measurements. Using a capillary having an inner diameter between 0.1 mm and 1 mm, preferably between 0.15 mm and 0.5 mm, and an outer diameter between 0.2 mm and 2 mm, preferably between 0.3 mm and 0.7 mm, has been found to be preferred for obtaining precise and sensitive measurements. In particular, an inner diameter as defined above is advantageous for ensuring a short path length of the light beam within the sample under study; in addition, the heat conduction between the vessel material (and thus the sample) and the heating element, preferably made of silicon, is better in case of small diameters. However, in the case of a DLS measurement, a larger diameter is considered to be better.

According to the method of the present invention, a monochromatic light source is provided, preferably a coherent light source such as a laser. Monochromatic light describes an optical radiation comprising a single optical frequency. As known in the art, no real laser is truly monochromatic and all lasers can emit light over some range of frequencies, known as the line width of the laser transition. In most lasers, the line width is quite narrow. Therefore, the present invention refers, for simplicity, to monochromatic light. Monochromatic light is especially advantageous for characterizing particles in solution as its use ensures defined, constant measurement conditions and thus, precise and highly accurate analyses.

Preferably, the light from the monochromatic light source has a wavelength of less than 500 nm, more preferably between 350 nm and 500 nm, even more preferably of 405 nm, 445 nm, or 488 nm. Measuring at wavelengths smaller than 500 nm such as at 445 nm, 405 nm, or 488 nm is especially advantageous for reducing costs while maintaining high quality of the results as cheaper laser and less complex laser can be used. Furthermore, using light from a monochromatic light source having a wavelength of less than 500 nm, such as at 445 nm, 405 nm, or 488 nm, has the advantage of resulting in stronger scattering light signals and lower absorption of most particles, including most proteins, compared to the use of light from a monochromatic light source having a wavelength of 500 nm or more.

Monochromatic light can be provided by a laser, wherein the laser is preferably a diode laser, and even more preferably a diode laser selected from the group consisting of frequency stabilized diode laser, DPSS laser, PPLN frequency doubled diode laser, frequency multiplied DPSS laser, diode pumped fiber laser, frequency multiplied diode pumped fiber laser, and diode pumped upconversion fiber laser. Preferably, the laser has a power between 1 mW and 200 mW, preferably between 10 mW and 100 mW, more preferably between 45 mW and 80 mW, even more preferably between 50 mW and 70 mW.

A monochromatic light source can be characterized by its coherence length. The coherence length is the maximum difference in path length, or transit time, that two light beams from the same monochromatic light source may have so that a stable interference pattern is created when they are superimposed. An interference pattern can result from interference effects, which can be caused by phase differences of the light waves arriving at the detector due to different path lengths and/or transit times of the light. The monochromatic light source, preferably a laser, has preferably a coherence length of at least 0.1 mm.

According to the method of the present invention, light from the monochromatic light source, preferably a laser, is transmitted to the vessel comprising the sample including the particles in solution under study. Thus, light is preferably transmitted as a light beam from a laser to the vessel comprising the sample under study for characterizing the particles in solution comprised in said sample. Herein, the terms "light", "light beam", and "beam" are used interchangeably.

Light can be delivered by several means. Preferably, the monochromatic light is delivered from the monochromatic light source via a single mode fiber. More preferably, the monochromatic light is delivered from a laser via a at laser wavelength single mode fiber, for example via a at laser wavelength polarization maintaining fiber.

The monochromatic light transmitted from the monochromatic light source to the vessel, i.e. the transmitted monochromatic light, is preferably focused in the vessel comprising the sample using an objective lens. Furthermore, the light emitted from the vessel is preferably also collected by said objective lens. Said objective lens has preferably a focal length between 10 mm and 200 mm. Alternatively or additionally, the transmitted monochromatic light is preferably focused in the vessel with a focal spot having a full width at half maximum (FWHM) between 3 μm and 30 μm, preferably resulting in a measurement volume that is smaller than the sample volume. In particular, a measurement volume that can be investigated using the method according to the invention is preferably between 0.01 nl and 0.1 nl, more preferably between 0.01 nl and 0.02 nl, and even more preferably about 0.016 nl.

Hence, it is especially preferred that monochromatic light is provided from a powerful laser via a wide aperture, e.g. an aperture having a width between 0.5 mm and 10 mm, preferably between 1 mm and 5 mm, that said light has a wavelength of 405 nm, 445 nm, or 488 nm and is focused in the vessel comprising the sample using an objective lens. Thus, e.g. about 1 million detected photons per second are transmitted to the vessel. For such cases, methods for measuring characteristics of particles in solution are known in the art. For ensuring accurate results, said methods use, e.g., an optical filter positioned between the light source and the vessel to reduce the amount of light transmitted to the vessel, and/or comprise a step of diluting the sample for reducing the concentration of particles in solution to reduce the amount of emitted light. Contrarily, the method according to the present invention can be applied without diluting the sample or using such a filter by providing at least two different analysis modes as explained below (cf. detailed description of obtaining and processing output signals).

For characterizing the particles in solution with high quality, it is of further relevance how the light is exactly transmitted to the vessel comprising the sample. More specifically, it is advantageous to position an optic obliquely to the capillary axis to avoid the detection of reflections from the vessel. Hence, light from the monochromatic light source is preferably transmitted to the vessel, e.g. the capillary, with a predetermined angle. In particular, light from the monochromatic light source is preferably transmitted to the vessel with an angle $\varphi_L$ to a longitudinal axis of the vessel, e.g. the longitudinal axis of a capillary, wherein $\varphi_L$ is preferably between 0 degrees and 45 degrees.

According to the method of the present invention, a light detector is further provided and used for detecting light emitted from the vessel, wherein the emitted light from the vessel refers to scattered light from the vessel, e.g. the capillary. Furthermore, the emitted light is preferably detected at a predetermined angle. Hence, light detected with the light detector is preferably emitted from the vessel, e.g. the capillary, with an angle $\varphi_D$ to a longitudinal axis of the vessel, e.g. capillary, wherein $\varphi_D$ is preferably between 0 degrees and 45 degrees. Preferably, the value of $\varphi_L$ is identical to the value of $\varphi_D$. Furthermore, an angle $\varphi_S$ between the light that is transmitted from the monochromatic light source to the vessel, e.g. capillary, and the light emitted or scattered from the vessel, e.g. capillary, that is detected with the light detector is preferably between 0 degrees and 150 degrees, preferably between 10 degrees and 150 degrees, more preferably between 10 degrees and 60 degrees.

As exemplarily shown in FIG. 1 A), light from a monochromatic light source such as a laser can be transmitted to a vessel 11, e.g. a capillary 11, including a sample comprising the particles in solution under study 12, as an excitation beam 50 with an angle $\varphi_L$ 53 to the longitudinal axis 10 of the vessel 11. The light of the excitation beam 50 is scattered by the particles in solution under study comprised in the sample 12 and thus, is emitted from the vessel 11. The emitted light or scattered light can be detected as a detected beam 51 at an angle $\varphi_D$ 20 to the longitudinal axis 10 of the vessel 11. The angle between the excitation (light) beam 50 and the detected (light) beam 51 is referred to as $\varphi_S$ 54 and can also be described as angle between the light that is transmitted from the monochromatic light source to the vessel 11 and the light emitted from the vessel that is detected with the light detector.

Figure 1B:
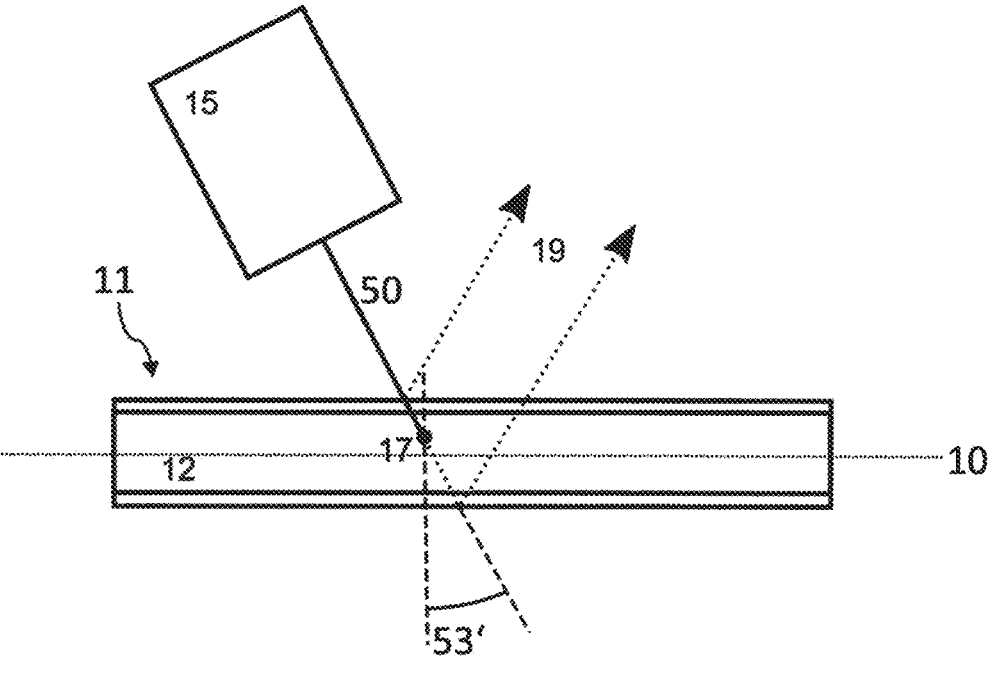

As exemplarily shown in FIG. 1 B), it is advantageous to position a DLS optics 15 such that the excitation beam 50 is transmitted at an angle $\varphi_L$ 53 to the longitudinal axis 10 of the vessel 11, e.g. obliquely to the capillary axis, to avoid detection of reflected light beams 19, which are reflected by the walls of the capillary 11. FIG. 1B) shows the angle 53' which is $90°-\varphi_L$. The present invention provides the advantage that the excitation beam 50 is focused to a focal point 17, which is located within the vessel, by using appropriate DLS optics 15. Thus, by using appropriate focusing optics and emitting the light in an appropriate angle with respect to the longitudinal axis 10 of the capillary, disturbing reflections from the capillary walls can be avoided. There are preferably no optical fibers between the optics 15 and the capillary 11 necessary, such that a small distance of air between the optics 15 and the capillary allows easier relative movement between the optics 15 and the capillary 11, which is advantageously in case a plurality of capillaries should be measured in a short time. Placing the focal point 17 inside the capillary can be achieved by strong focusing with a small focal length.

In particular, to ensure that the focal point 17 is within the small capillary, the present invention provides a method for an enhanced measurement of the location of the capillary and optionally a feedback control to reposition the capillary and/or the position for the measurement and/or subsequent measurements. Moreover, according to the present invention it is not only possible to ensure that the measurement is (somewhere) inside the vessel, it is further preferred to measure at the best spot inside the vessel.

For instance, in case the vessel is a capillary, such a capillary typically has an inner diameter of 500 μm, but the size, for example the diameter, of the preferred spot is only ~50 μm. With the above-mentioned focusing means, 10 μm accuracy is achievable. Based on said high accuracy, not only the position of the vessel/capillary can be precisely determined but also a measurement volume within the vessel, e.g. a volume which is located somewhere "in the middle" of the vessel which is located by some distance from the vessel wall(s).

Figure 14:
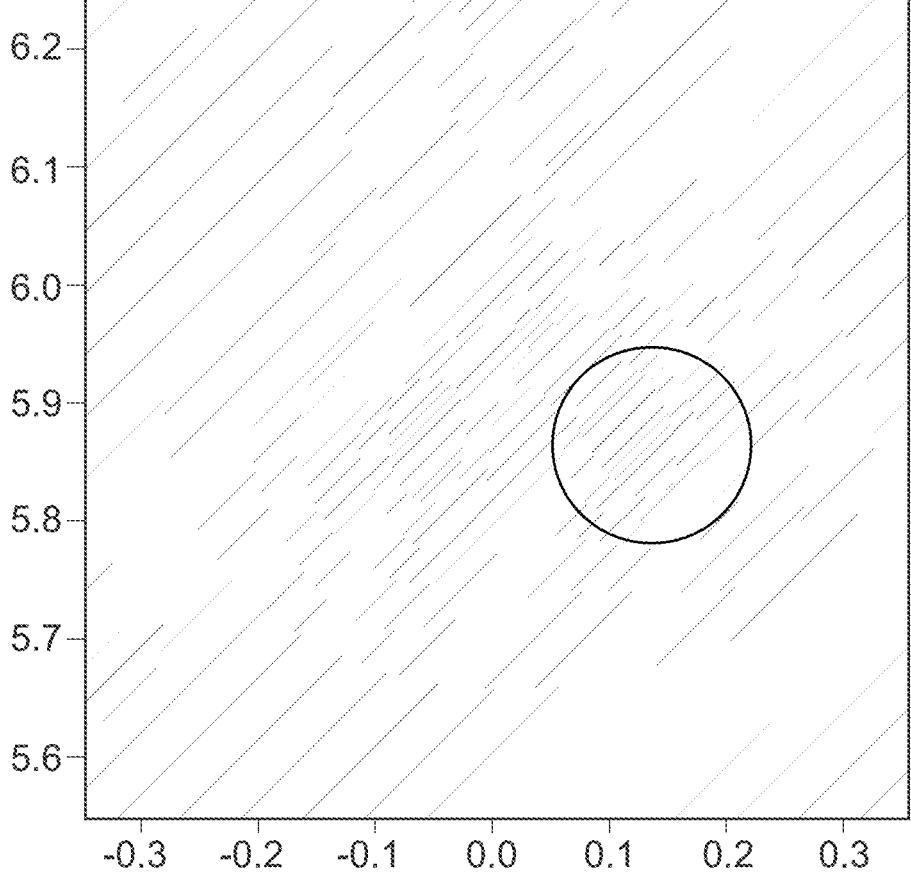
FIG. 14: Illustrates the signal quality of a DLS measurement at different positions within a vessel to determine the optimal measuring spot within the vessel.

This location or spot can be found, e.g. by performing multiple DLS measurements at different positions inside the vessel/capillary, using a weakly scattering sample. The preferred spot is the one with the highest SNR of the autocorrelation function (SNR=(amplitude of acf)/(sum of squared fit residuals)). For instance, FIG. 14 shows a scan of a capillary with different values of SNRs in different colours, which allows, e.g., to identify the encircled region as the spot for the measurement. As example a typical value of the SNR is 50 when using a lysoszyme sample of concentration 2 mg/ml and a measurement duration of 200 ms.

The provided light detector is preferably a photomultiplier tube (PMT), a silicon photomultiplier (SiPM), or an Avalanche photodiode (APD) photon counting detector. The raw output signal of such a detector is typically an analog output signal, e.g. a variable current or voltage, which can be converted into variable voltage or current, respectively. According to the present invention, said variable output signal is preferably further processed as discussed in further detail below. In contrast, conventionally, DLS measurements are limited by using APD photon counting detectors only. However, APD photon counting detectors have the disadvantage that the intensity of the detected light must be weak in order to be able to be detected. Some state-of-art devices try to overcome this disadvantage by using for example additional filters for reducing the intensity of the light which takes time and thus, reduces throughput. Hence, to overcome these drawbacks the light detector of the present invention is preferably a PMT or a SiPM which provide further advantages, as discussed in further detail below.

According to the method of the present invention, the light detected by the light detector can be used for a dynamic light scattering measurement and thus, characteristics of the particles in solution comprised in the sample can be determined based on a DLS measurement. For a given sample, the DLS measurement is preferably obtained in less than 5 sec, more preferably in less than 1 sec, preferably in between 200 ms to 800 ms, more preferably in about 500 ms. Thus, high throughput can be ensured while ensuring high accuracy and sensitivity of the analysis even in case of small sample volumes under study.

The DLS measurement preferably comprises a step of performing at least one correlation operation, preferably at least one autocorrelation operation. An autocorrelation operation (or function) evaluates the similarity of a signal at a given time with the signal after a certain delay time, wherein fluctuations in intensity are slower for large particles than for smaller particles. Hence, an autocorrelator calculates the normalized autocorrelation function describing the similarity of the signal after certain delay times and thus, correlates intensity fluctuations of scattered light with respect to time to determine how rapidly the intensity fluctuates, which is related to the diffusion behavior of particles. Thus, a step of performing at least one correlation operation, preferably at least one autocorrelation operation, is advantageous for determining the diffusion coefficient of the particles in solution based on the fluctuations of the light intensity arriving at the detector. Preferably, the respective correlation, preferably autocorrelation, function(s) is transferred to a PC for further analysis and/or stored on a storage medium such as a hard disk.

The DLS measurement preferably comprises the steps of obtaining an analog output signal obtained from the light detector; and of processing the obtained analog output signal. Preferably, the step of processing the obtained analog output signal comprises the step of digitalizing the obtained analog output signal into a digitalized output signal. In particular, the obtained analog output signal can be digitalized into a digitalized output signal with different data rates, preferably with a high data rate of at least 40 MS/s. This is especially advantageous in case of the provided light detector being a PMT or a SiPM, which can thus even be used in continuous operation according to the method of the present invention.

Preferably, the step of processing the obtained analog output signal into a digitalized output signal further comprises the step(s) of i) processing the digitalized output signal as a digitalized single photon pulse signal, preferably in case the intensity of the detected light emitted from the vessel is below 2 million detected photons per second; and/or ii) processing the digitalized output signal as discrete values of an analog signal, preferably in case the intensity of the detected light is above 2 million detected photons per second. This has the advantage that the obtained analog output signal can be processed dependent on the signal intensity and/or signal intensity fluctuation of a sample, thus ensuring an optimal processing of the obtained analog output signal and an optimized characterization of the particles in solution comprised in the sample under study.

In particular, photons emitted from the vessel comprising the sample under study can be detected by a light detector such as a PMT and the obtained analog output signal is preferably digitalized.

Hence, in case the intensity of the detected light emitted from the vessel is below 2 million detected photons per second, the digitalized signal of said low scattering sample is preferably processed as a discretized signal and thus, as a digitalized signal. Thus, individual photons emitted from the vessel can be detected with high precision. The advantage of counting single photons in the low brightness range is based on the knowledge that all photons have the same energy content and thus (all) other signal parts can be inferred as being noise or caused by other random factors such as offset drift and/or gain fluctuations.

Figure 2:
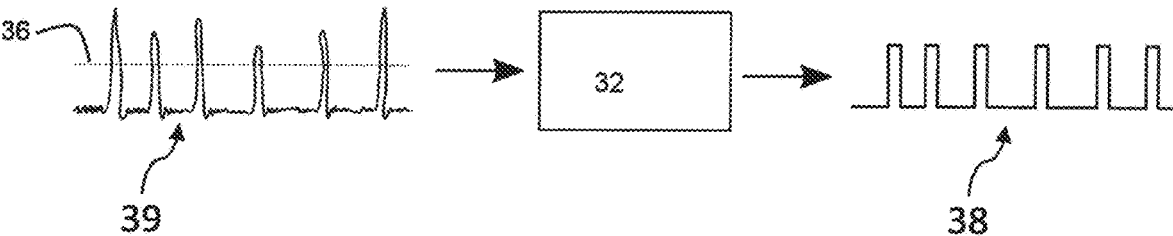
FIG. 2: Functionality of the pulse discriminator.
Figure 4A:
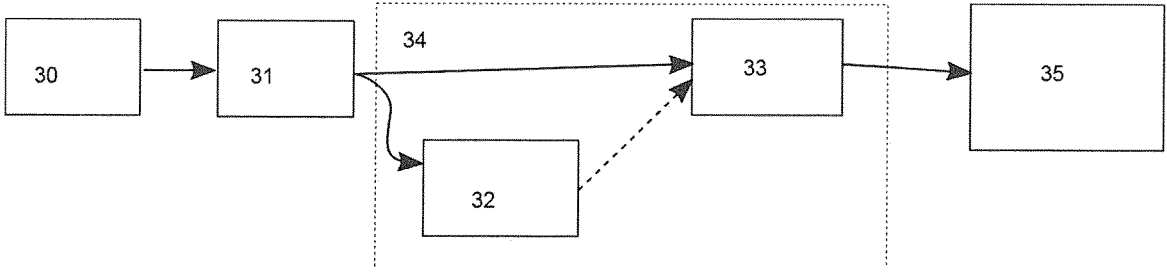
FIG. 4: A) Signal plan with a correlator whose input is switched between photon counting and analog data. B) Signal plan with two parallel running correlators, one in analog mode, the other in photon counting mode.
Figure 4B:
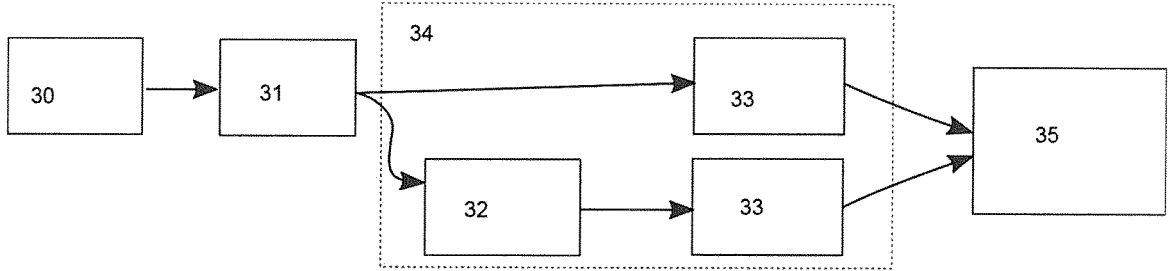

Single photons can be counted for example by using a pulse discriminator. As discussed in further detail with regard to FIGS. 4A and 4B, it is preferred that the analog output signal (directly) coming from the detector 30 is digitized, preferably by an ADC. An example of a resulting digitalized output signal 39 is shown on the left side of FIG. 2. In particular, the illustrated signal 39 is a digitalized output signal of a PMT. As also exemplarily shown in FIG. 2, a pulse discriminator 32 can be used for discretizing the digitalized output signal 39, e.g. obtained from a light detector after digitalization, by applying a threshold value such as a photon counting threshold value 36. Thus, in case the digitalized output signal exceeds the threshold value 36, a discretized signal is created that indicates, e.g., the presence of a photon. In other words, digitalized output signal 39 is processed as digital (single) photon pulse signal. If the signal 39 does not exceed the threshold value, the respective discretized signal indicates, e.g., the absence of a photon.

However, when the obtained signal becomes too bright and thus, too many photon signals overlap, e.g., single photon counting is hardly or not possible. In this case, the digitalized output signal is preferably processed "as an analog signal", e.g., as discrete values of an analog signal. Still in other words, said digitized signal provides a continuous signal which can be processed similar as an original analog signal. In the present application, it is also referred to the step of processing the digitalized output signal as discrete values of an analog signal with discrete values. The latter option is preferably used in case the intensity of the detected light is above a certain threshold, e.g., above 2 million detected photons per second or the respective brightness value according to quantization depth after digitization for example. In case of the light detector being a SiPM, a digitalized output signal may even be processed as a digitalized signal in case of an intermediate brightness level, for example an intensity of the detected light between 2 million detected photons per second and 6 million detected photons per second, by discretization of the photon peak area and thus, the amount of actually detected photons can be estimated.

The step of processing the obtained analog output signal and the subsequently produced digitalized output signal preferably comprises either step i) or step ii). Thus, the digitalized output signal is preferably processed either as a digitalized single photon pulse signal or as discrete values of an analog signal. For deciding whether to process the digitalized output signal according to i) or ii) a field programmable gate array (FPGA) is preferably used. Using for example an FPGA, switching between photon counting and analog operation can be done in microseconds. Thus, the time to decide whether to process the digitalized output signal as a digitalized signal according to step i) is preferably less than 1 sec, more preferably maximal 0.05 sec, e.g. using an FPGA. The algorithm of the FPGA preferably runs as some kind of "software" on the FPGA. Said algorithm (software) for processing the data can be changed, for example with an update. In other words, a change of specifications/algorithms of the signal processing via a software update is easily possible. Hence, a change of the hardware/detectors is not necessary which provides a great advantage.

According to the present invention it is also possible to process the digitized output signal simultaneously according to i) and ii). Like this, the decision whether to process according to step i) or ii) can be met after the measurement.

Figure 3:
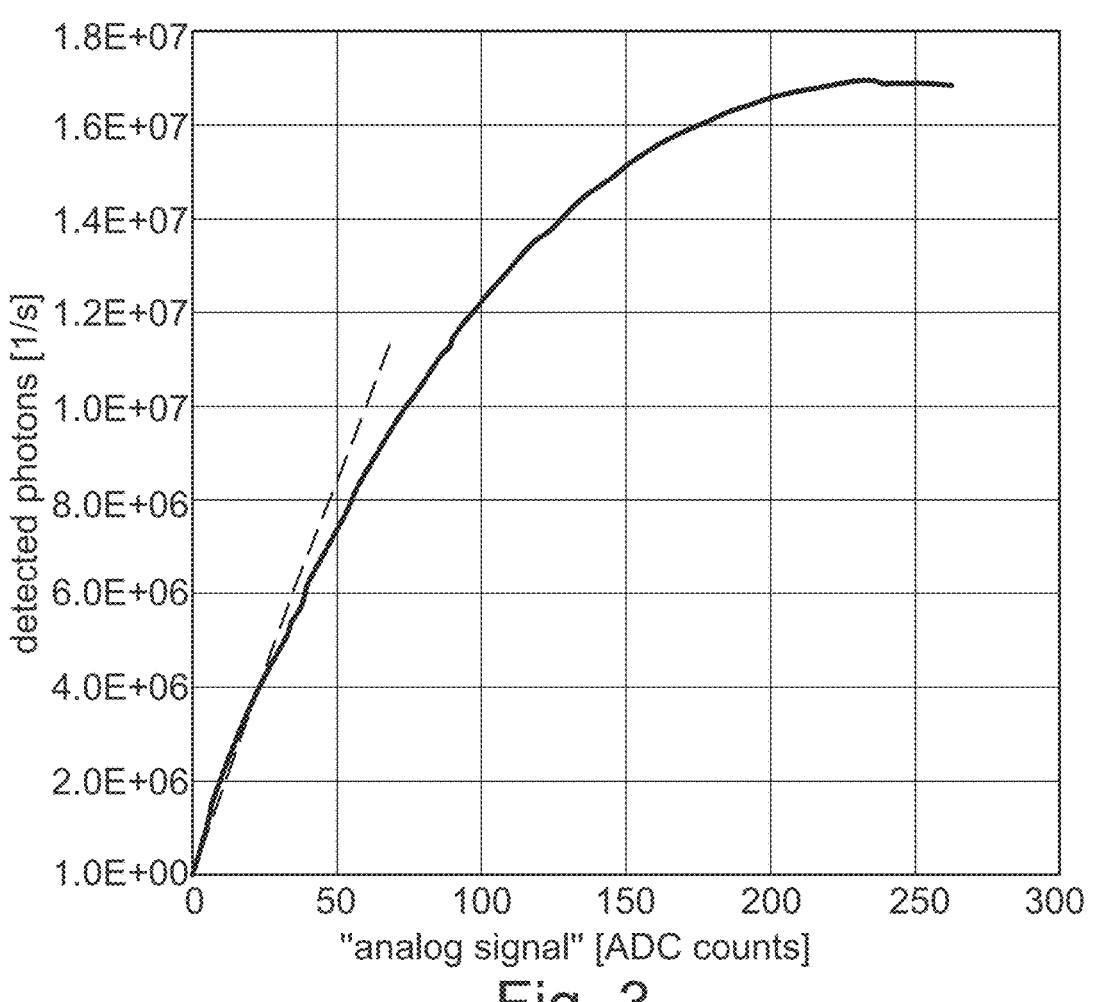
FIG. 3: Signal strength of a photon counting signal plotted over the signal strength of an analog signal (dashed line indicates an extrapolated fit of the linear range).

The advantage of deciding whether to process the digitalized output signal according to i) or ii) is exemplarily shown in FIG. 3 which depicts the signal strength of a photon counting signal plotted over the signal strength of an analog signal, wherein the dashed line indicates an extrapolated fit of the linear range. Briefly, a PMT was irradiated using an LED with a very low power and a signal was measured within a few milliseconds. The in FIG. 3 shown "analog signal" represents an average value of said signal, whereas the shown "detected photons/second" signal was obtained by counting the number of photon peaks in the respective measuring interval and scaling it to one second. Then, the LED power was increased and the measurement repeated.

Hence, as shown in FIG. 3, at a certain radiation power more and more photon peaks overlapped and were no longer recognized as separate peaks. More specifically, at some point the photon signal no longer increased proportionally with the LED power. Conventional DLS instruments measure in the photon counting range and thus, comprise filters that are put in the light beam path in case the signals are too strong, i.e. the number of detected photon counts becomes too high. Contrarily, the DLS measurement according to the present invention comprises analyzing the digitalized output signal as a "photon-counting signal" in case the linearity error is below, e.g., 5%, i.e. in the example shown in FIG. 3 above approx. $3*10^6$ photons per second or 20 counts mean analog signal, whereas at higher powers the digitalized output signal is analyzed as an analog signal. Hence, using the method and the device according to the invention has the advantage of reduced DLS measurement times and thus, increased throughput due to an intensity dependent signal processing as described above.

Alternatively, both processing options may also be applied in parallel, wherein the term "parallel" is intended to be understood as "with a time offset of less than 1 ns". This is preferably achieved by using for example two processors in parallel (synthesized preferably in the same FPGA). Thus, the digitalized output signal may also be processed as a digitalized and an analog signal and the obtained data stored. This has the advantage that both processed digitalized output signals can be stored and processed at a later stage. Hence, the step of processing the obtained analog output signal may further comprise the steps of storing the processed digitalized output signals obtained from step i) and step ii), and further processing one of the stored output signals.

The steps from the emitted light to the processed signal may be shortly summarized as follows. The laser light emitted from the fiber can be directed in parallel via a collimator lens and focused into the vessel, e.g. capillary, via an objective lens. The beams of the scattered light and thus, the emitted light from the vessel, can be focused via the same or a further, preferably the same objective lens, through a further collimator lens to a fiber of the DLS detector as a light detector and can then be detected by a PMT. Since the PMT has in most cases a current output, whereas for the analog to digital converter (ADC) a voltage signal is usually required, an amplifier might be placed between the PMT and the ADC such that the current from the PMT can be converted into a voltage signal and amplified. The ADC may further convert the amplified voltage signal with a sampling rate of, e.g., 40 MS/s (40 million samples per second), into a digital signal with, e.g., 16 bit resolution. An autocorrelator that is preferably programmed with the FPGA can be used in real time to compute the autocorrelation function of the intensity signal, which can then be evaluated, e.g., using a computer.

In more detail, the step of processing the obtained analog output signal is exemplarily described with reference to FIGS. 4 A) and B). Thus, a light detector used for a DLS measurement, i.e. a DLS detector 30, can detect light emitted or scattered from a vessel comprising a sample under study. The analog signal obtained by the DLS detector is preferably converted into a digital signal, i.e. digitalized in the digitalized output signal, e.g. using an analog to digital converter (ADC; 31) and further transmitted to a field programmable gate array (FPGA; 34). The FPGA 34 may comprise one or more correlators that perform at least one correlation operation, preferably at least one autocorrelation operation. The FPGA 34 can comprise one correlator 33 as exemplarily shown in FIG. 4 A). In this case, the FPGA preferably comprises further a pulse discriminator 32 and the input signal for the correlator 33 can be switched between photon counting data obtained from the pulse discriminator 32 and digitalized data handled as analog data. Alternatively, the FPGA can comprise two correlators 33 running in parallel, one in analog mode, the other in photon counting mode based on the signal converted by a pulse discriminator 32 as exemplarily shown in FIG. 4 B). In all cases, the output of the one or more correlators 33 comprised in the FPGA 34 are preferably transferred to a PC 35 for further analysis and/or stored on a storage medium such as a hard disk.

Thus, the step of processing the obtained analog output signal preferably further comprises the steps of digitalizing the analog output signal into a digitalized output signal and storing the processed digitalized output signal obtained from step i) or step ii), preferably on a storage medium such as a hard disk.

The method according to the present invention preferably comprises a further step of measuring fluorescence. Preferable fluorescence of the particles in the solution comprised in the sample are used for the fluorescence measurement, wherein said fluorescence is preferably an autofluorescence of said particles. Measuring the fluorescence, preferably the autofluorescence, of particles in solution may be advantageous. The absence of any autofluorescence indicates a missing vessel or an empty vessel without fluorescent or autofluorescent. If this is the case, any (further) measurement, i.e. a DLS measurement and preferably a further fluorescence measurement such as a nano-DSF measurement, may be omitted. Hence, using information on the presence or absence of autofluorescence may be advantageous to reduce the time required for characterizing particles in solution using the method according to the present invention. Moreover, information about the signal intensity and/or signal intensity pattern of the detected autofluorescence signal can be obtained. This type of information is especially advantageous as the thus obtained information can for example be used for determining the position of the vessel comprising the sample with particles in solution that can emit fluorescence upon excitation with light and/or a nano-DSF measurement, and/or for detecting samples comprising contaminants without autofluorescence such as gold particles. Fluorescence is preferably measured by providing a further light source such as an LED, transmitting light from said further light source to the vessel comprising the sample, thus exciting autofluorescence of the particles, and detecting the emitted light from the vessel. Preferably, the further light source provides light with a wavelength of about 280 nm for excitation of autofluorescence of particles in solution, preferably of proteins in solution.

Herein, the term "fluorescence" refers to electromagnetic radiation including a release of energy in form of emission of electromagnetic radiation, e.g. in case of particles being excited by absorption of a photon. More specifically, particles such as proteins can exhibit autofluorescence, also referred to as intrinsic fluorescence, in case they comprise for example at least one of three specific aromatic amino acids, i.e. phenylalanine, tyrosine and tryptophan. The autofluorescence of proteins can be dominated by tryptophan, which has a higher extinction coefficient compared to tyrosine and phenylalanine. An extinction coefficient, also referred to as molar absorption coefficient, refers to a measure of the attenuation, i.e. extinction, of electromagnetic radiation by a medium, and is affected by the path length through the medium and by the concentration of the particles in solution, wherein a weakening can be caused by scattering and absorption. The absorption maximum of tyrosine and tryptophan is at a wavelength of about 280 nm with tyrosine exhibiting a lower dependence of the emitted wavelength on its position in a particle such as a protein compared to tryptophan. Thus, excitation of autofluorescence of particles such as proteins is preferably done with light, preferably from the further light source, having a wavelength of about 280 nm or 278 nm. For instance, an LED having a maximum intensity at about 270 nm to 290 nm, but for example, 278 nm, 280 nm or 285 nm is preferable to enhance efficacy.

The step of measuring fluorescence of the particles in solution is exemplarily described in more detail with reference to the upper panel of FIG. 5. As exemplarily shown in said upper panel of FIG. 5, fluorescence of particles in solution comprised in a sample 12 in a vessel such as a capillary 11 can be measured for example using fluorescence optics 14 with a predetermined fluorescence focus 16. The vessel and/or the optics 14 can be positioned such that the fluorescence focus 16 is located within the vessel for measuring fluorescence of the sample comprising the particles in solution 12. Upon measuring fluorescence, the vessel can be transferred to another position such that the DLS focus 17 of a DLS optics 15 is located within the vessel for performing a DLS measurement, wherein the fluorescence focus and the DLS focus are located in a predetermined x-distance to each other 18. Alternatively, the position of the vessel comprising the sample can remain the same during the fluorescence and the DLS measurement and the fluorescence optics 14 and the DLS optics 15 are therefore positioned in relation to the vessel respectively. Hence, the vessel, e.g. capillary, preferably moves relative to the optics 14 and 15. As a further alternative, both measurements may be performed simultaneously.

As the vessel is to be specifically positioned in relation to an optics such as a DLS optics for an accurate and reproducible measurement, it is advantageous to ensure a precise positioning even upon movement of the vessel between measurements. Hence, the method according to the present invention preferably comprises further the step(s) of determining the position of the vessel based on the measured fluorescence, and optionally positioning the vessel based on the measured fluorescence and the determined vessel position. Thus, the position of a sample can be accurately determined based on the measured fluorescence, e.g. based on the fluorescence of the vessel and/or the particles in solution comprised in the sample under study. This is especially advantageous if several samples are to be measured with high throughput. In this case, manual filling of a device with capillaries, which are often placed in a capillary holder, is not possible. Furthermore, for obtaining reproducible results of a measurement with high quality, the measuring position in the respective capillary must be located quickly. This can be achieved by determining the capillary position based on a fluorescence scan that is preferably performed prior or in parallel to the DLS measurement, preferably in parallel to the DLS measurement. Thus, for example 48 capillaries can be measured in approximately 2 seconds using the method according to the present invention. Conventional solutions are based on the detection of a scattered light signal of a sample container such as a capillary holder. However, signals obtained from a fluorescence measurement are generally stronger than from scattered light. Hence, using such a fluorescence scan is furthermore advantageous as it allows more accurate locating and optionally (re-)positioning of a capillary compared to said conventional solutions.

The thermal stability of a particle such as a protein can be analyzed using a melting curve, which represents the change in fluorescence as a function of temperature. More specifically, by forming the first derivative of the melting curve, the melting point $T_m$, i.e. the temperature at which half of the particles are denatured, can be determined. Thus, a sample can be heated by applying a temperature ramp for example from 15° C. to 95° C., preferably 20° C. to 90° C., with a heating rate between 0.1° C./min and 7° C./min.

Hence, the method according to the present invention preferably comprises a further step of tempering the vessel over time at least with a first temperature at a first time point and a second temperature at a second time point. Preferably, said step of tempering the vessel over time comprises tempering the vessel with a tempering rate between 0.01° C. per minute and 30° C. per minute, preferably between 0.1° C. per minute and 10° C. per minute, and/or wherein the first temperature and the second temperature are between −20° C. and 160° C.

The method according to the present invention preferably further comprises the step of performing a nano differential scanning fluorimetry (nano-DSF) measurement. Performing a nano-DSF measurement is advantageous for analyzing conformational changes of a particle, preferably of a protein. nano-DSF is preferably measured by providing a further light source such as an LED, transmitting light from said further light source to the vessel comprising the sample and detecting the emitted light from the vessel. Preferably, the further light source provides light with a wavelength of about 280 nm for excitation of particles in solution, preferably of proteins in solution. The further light source for transmitting light to the vessel for performing a fluorescence measurement, e.g., as used for the determination of the positioning of the vessel and for performing a nano-DSF measurement, respectively, can be the same further light source or a different further light source.

A nano-DSF measurement is based on the dependence of the emission spectrum of the protein and on the position of the tryptophan within said protein. Tryptophan is an aromatic amino acid which is mostly located in an inner part of a protein in its native conformation. However, if a protein loses its native conformation for example due to denaturation, inner parts of the protein are exposed to a more polar environment. As the emission spectrum of tryptophan depends on its environment, a loss of the native conformation of a protein can result in the exposure of tryptophan to a more polar environment, which results in a shift of the emission maximum of approximately 325 nm in a nonpolar environment to a longer wavelength range of approximately 350 nm. Hence, information on the environment-specific emission spectrum of tryptophan can be used for analyzing conformational changes of a protein. Therefore, fluorescence of a protein can be excited with a wavelength of about 280 nm, the resulting emission detected at about 350 nm and 330 nm, and a quotient formed based on the intensities of fluorescence at about 350 nm and 330 nm, which usually increases due to denaturation. Denaturation of a protein can occur due to chemical and/or thermal denaturation conditions including an increase in temperature.

A nano-DSF measurement is preferably performed upon exposing particles in solution to varying temperatures, for example using a temperature ramp and thus, upon tempering a vessel comprising the particles in solution under study over time with at least a first temperature at a first time point and a second temperature at a second time point. This is especially advantageous to obtain information about the conformational changes of a particle in solution under study depending on the temperature said particles are exposed to.

The incorporation of a nano-DSF measurement into the method of the present invention is exemplarily described in more detail with reference to FIG. 5. As exemplarily shown in the upper panel of FIG. 5, fluorescence of particles in solution comprised in a sample 12 in a vessel such as a capillary 11 can be measured for example using a fluorescence optics 14 such as a nano-DSF optics with a predetermined fluorescence focus 16. The vessel can be tempered using a tempering element which can heat and/or cool the vessel, e.g. capillary, e.g. a heating pad/bed and the emitted fluorescence of the particles in solution measured for a given temperature using DLS and a fluorescence measurement such as nano-DSF. Therefore, the vessel, tempered at a first temperature, is positioned such that the fluorescence focus 16 is located within the vessel for measuring fluorescence of the sample comprising the particles in solution 12. Upon measuring fluorescence, the vessel can be transferred to another position such that the DLS focus 17 of a DLS optics 15 is located within the vessel for performing a DLS measurement, wherein the fluorescence focus and the DLS focus are preferably located in a predetermined x-distance to each other 18. Alternatively, the position of the vessel comprising the sample can remain the same during the fluorescence and the DLS measurement and the fluorescence optics 14 and the DLS optics 15 are therefore positioned in relation to the vessel respectively. As a further alternative, both measurements may be performed simultaneously. After a DLS and a fluorescence measurement are performed at a given temperature (as indicated in the middle and lower panel of FIG. 5), the temperature of the sample is for example increased by increasing the temperature of the tempering element 13, which is located in close proximity to the vessel. Once the sample is tempered at a second temperature, another round of DLS and/or fluorescence measurement can be performed as described above. Thus, the particles in solution comprised in the vessel can be characterized in dependency of the temperature by tempering the vessel comprising the sample over time at least with a first temperature at a first time point and a second temperature at a second time point and performing at least a DLS and a fluorescence, preferably a nano-DSF, measurement per time point.

Alternatively, or additionally, the method according to the present invention preferably comprises a further step of measuring back-reflection of the vessel comprising the sample. Back-reflection is preferably measured by providing a further light source such as an LED, transmitting light from said further light source through the vessel comprising the sample and detecting the light that gets reflected e.g. by a mirror below the vessel (cf. e.g. FIG. 11). Thus, depending on the intensity of the measured back-reflected light it can be deduced whether a vessel and/or a sample is present and/or information can be obtained on the position of said vessel and/or sample. More specifically, the intensity of the measured light that is back-scattered, e.g. by a mirror below the intended vessel position, is stronger in case no vessel is provided than in case a vessel is provided. Furthermore, once a vessel is provided the intensity of the back-reflected light differs between an empty vessel, a vessel comprising a fluid without particles under study and/or comprising contaminants, and a vessel comprising a sample according to the present invention, respectively. Hence, measuring back-reflection can be advantageous for detecting a vessel and/or sample and/or obtaining information on the respective exact position. Moreover, if the sample is provided and at least partially aggregated, the aggregated particles comprised in the sample scatter part of the light in directions outside the receiving cone of the light detector; the stronger the aggregation, the weaker the detected signal. Thus, information on the presence and/or intensity of particle aggregation can be obtained by measuring back-reflection, which is advantageous for reducing the time required for performing the method according to the present invention and for increasing the accuracy of the same.

Preferably, the further light source provides light with a wavelength of about 385 nm for excitation of particles in solution, preferably of proteins in solution. Preferably, light at a wavelength of about 385 nm is furthermore detected for a back-reflection measurement. An LED emitting light with the desired wavelength is preferred, e.g., an LED with a maximum intensity at about 385 nm. The further light source for transmitting light to the vessel for performing a fluorescence measurement, a nano-DSF measurement, and/or a back-reflection measurement, respectively, can be the same further light source or a different further light source. Measuring back-reflection is advantageous for investigating colloidal stability of particles in solution such as proteins.

For an analysis using back-reflection, a sample comprising the particles in solution and hold by a sample holder is irradiated with a light beam, e.g. with a wavelength of 385 nm, such that the light beam is reflected by the material of the tempering element below the vessel in case the light source is positioned above the vessel and crosses the sample another time. For instance, a tempering element made from silicon can be used for tempering and providing a reflective surface. Since larger particles including particle aggregates scatter the light stronger than smaller particles, the reflected light is attenuated stronger in case of larger particles. Thus, the intensity of the reflected light provides qualitative information about the presence of larger particles including particle aggregates in a sample under study.

According to a preferred embodiment, a tempering element is made from silicon (Si), which provides certain advantages, e.g., Si provides a smooth surface, good thermal conductivity, good mechanical and chemical stability and good reflectivity. Preferably the vessel to be tempered is in direct contact with said tempering element. Silicon does also not have autofluorescence, which could disturb the positioning determination of the vessel by fluorescence, as preferably done by the present invention. The silicon tempering element may be formed, for example, from a portion of a silicon wafer. According to a further embodiment a tempering element can be used in which the surface being in contact with the vessel is modified in such a way, for example with an interference coating, that it reflects the wavelength of the light used for the back-reflection and/or the fluorescence measurements and that it does not reflect (for example instead absorbs and/or transmits) the light used for the DLS measurements. For example, it is preferred to reduce the reflectivity at approximately 405 nm, preferably at 400 nm±10 nm.

Moreover, by measuring the change in intensity of reflected light for example during a temperature ramp, the onset of aggregation ($T_{agg}$) can be determined, which indicates the temperature at which the size of the particles in solution increases due to the onset of aggregation. Hence, back-reflection is preferably measured while tempering the vessel over time as described to obtain information about colloidal stability and temperature-induced aggregation of particles in solution.

Furthermore, there is an advantageous effect arising from the combination of the back-reflection technology and DLS as explained in more detail in the following section. DLS and back-reflection complement each other well and can extend the measuring range of the device and method according to the present invention considerably. In particular, the usefulness of DLS is limited for "dirty" samples, e.g. cloudy ones, whereas the back-reflection technology works well for such samples. On the other hand, the back-reflection technique is not sensitive enough to detect small particles with high quality whereas high quality measurements can be obtained from DLS for such samples. Moreover, sometimes there are a lot of PEG molecules in pharmaceutical formulations which are used to stabilize the actual active substance, but these molecules can cause such a strong scattering signal that DLS can become saturated and therefore "blind". Thus, the back-reflection measurement can be compared with a "turbidity" measurement and is very robust: if aggregated particles are large and/or frequent (e.g. sample failed and/or looks "milky") then the DLS optic can become saturated, thus of less use, whereas the back-reflection optic can still measure with high quality. This is not possible with any other device and allows furthermore an extremely large measurement range.

As an example: in case an antibody is investigated using capillaries and starting at 20° C., then DLS, nano-DSF and back-reflection can be measured with high quality, even when heating up the sample with 1° C. per minute up to an "inflection temperature" (i.e. "melting temperature") of a certain antibody domain. Once the melting temperature is reached, the antibody starts to aggregate. However, up to an "inflection temperature" +5° C. DLS, nano-DSF and back-reflection can still be measured with high quality. However, starting from an "inflection temperature"+5° C., the antibody aggregates so strongly and starts to precipitate that the DLS optics can become saturated/blind, while nano-DSF and back-reflection produce interpretable data. However, the back-reflection optics may give a scattered light signal because it is less sensitive, but still the turbidity of the sample can be measured with high quality. Accordingly, the combination of these measurement in the same sample at substantially the same time provides an enhanced determination of characteristics of the sample.

The size of particles in solution such as proteins can furthermore be determined using for example a static scattering light measurement, which has the advantage of having a wide measuring range. For a static scattering light measurement, light from a monochromatic light source such as a laser is transmitted to a vessel comprising the sample under study and the light scattered by the particles in solution comprised in the sample is measured by at least two light detectors at different angles. Thus, the method according to the present invention preferably further comprises the step of providing a further light detector and measuring static scattering light of the vessel comprising the sample using the further light detector, preferably with an angle φ to a longitudinal axis of the vessel, wherein φ is preferably between 10 degrees and 150 degrees, more preferably between 10 degrees and 60 degrees.

The method according to the present invention is preferably applied to more than one sample comprising particles in solution under study for measuring characteristics of particles in solution with high throughput. Hence, it is preferred that a plurality of vessels is provided, wherein each vessel comprises a sample of particles in solution, and wherein characteristics of particles in solution are measured for each vessel as described herein. Thus, the method according to the present invention can be used to characterize particles in solution with high throughput using more than one vessel, wherein the same particles in solution are comprised in each vessel though under another experimental condition such as a different detergents concentration. Alternatively or additionally, the method according to the present invention can be used to characterize different particles in solution with high throughput by providing a plurality of vessels with said vessels comprising each a sample of different particles in solution.

Moreover, in case the method according to the present invention is applied to a plurality of vessels as described above, it is preferred that i) a fluorescence measurement for each vessel is followed by a DLS measurement for each vessel; or that ii) a DLS measurement for each vessel is followed by a fluorescence measurement for each vessel; or that iii) a fluorescence measurement and a DLS measurement is performed for one vessel of the plurality of vessels followed by a fluorescence measurement and a DLS measurement for another vessel of the plurality of vessels. Preferably, a fluorescence measurement is performed that is followed by a DLS measurement. This is especially advantageous as information from the fluorescence measurement can be used in addition for accurately locating and optionally (re-)positioning the respective vessel for the DLS measurement and hence, for ensuring reproducible high-quality results of the DLS measurement. More preferably, a fluorescence measurement is simultaneously performed with a DLS measurement for each vessel of the plurality of vessels.

Example of a Preferred Embodiment

Preferably, the method according to the present invention comprises at least the above in detail described steps of detecting a florescence signal of a vessel, determining the exact position of the vessel, optionally (re-)positioning the vessel relative to the light source and/or optics, performing a DLS measurement, preferably further a nano-DSF measurement, at a first temperature, tempering the vessel, detecting a florescence signal of the vessel, determining the exact position of the vessel, optionally relative (re-)positioning the vessel, performing a DLS measurement, preferably further a nano-DSF measurement, at a second temperature, etc. Thus, three-dimensional structure, particle size distribution and aggregation of particles and their dependency on a parameter such as temperature, can be assessed comparatively cheap, fast and with high reproducibility and accuracy. Moreover, the method according to the present invention comprising at least said steps is preferably performed using more than one vessel. This has the advantage of obtaining precise measurements results with high throughput.

Figure 11:
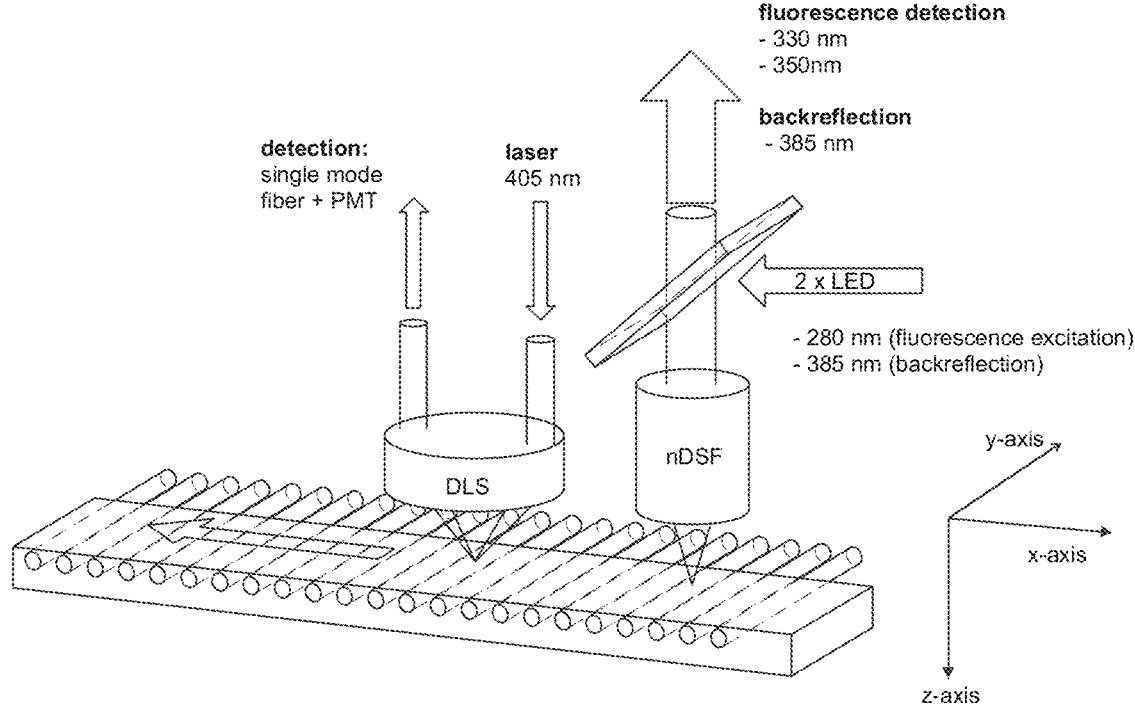
FIG. 11: Scheme of a preferred embodiment of the present invention.

A preferred example of a measurement cycle according to the present invention will be described in more detail in the following with reference to FIG. 11. In particular, the measurement is exemplified using a capillary as a vessel, wherein the sample comprising the particles under study is drawn into the vessel by the capillary force. The capillary might then be placed on a sample carrier/holder. According to another embodiment, a plurality of capillaries is mounted on a holder and the plurality of capillaries can be filled simultaneously by inserting one end of each capillary in different samples, e.g., inserting the plurality of capillaries simultaneously into respective wells of a multiwell plate. According to a preferred embodiment, 1 to 48 capillaries are provided on the sample carrier/holder. It is further preferred that the temperature of these plurality of capillaries/vessels (see FIG. 11) can be controlled very precisely to a specific temperature. For instance, a tempering means can be provided so that all capillaries at a temperature of e.g. 75° C. are within a temperature range of 75° C.+/−0.2° C. "homogeneity". This means that all, every single capillary has practically the same temperature and so the capillaries are comparable with each other. This precisely controlled temperature for a plurality of capillaries/vessels allows, e.g., isothermal measurements or temperature ramp measurements. For instance, in an isothermal mode, all samples are maintained at a single temperature within a precision of +/−0.5° C. [please specify, a precision of +/−0.2° C. for a specific time, e.g., more than 1 minute, more than 2 minutes, more than 1 hour, more than 1 day, up to 7 days. The precisely controlled temperature also allows a temperature ramp mode, e.g. tempering the samples in the plurality of capillaries from 20° C. to 95° C. with a heating rate of 1° C. per minute. At ambient temperature, all capillaries have substantially the same temperature. With the present invention, however, it is possible to maintain the specified precision at temperatures across all capillaries at all temperatures of the temperature ramp.

The measurement is preferably performed in such a way that the sample carrier is moved in the x-direction so that the signal of all vessels can be detected successively by the respective optics, e.g. for a DLS and/or nano-DSF measurement. Alternatively, the light source, the detector and/or the respective optics may be moved with respect to the sample carrier. According to a further embodiment, the carrier and the light source, detector and respective optics may be moved. In other words, it is preferred that there is a relative movement between the vessel and the detection system. When the sample carrier is moved in the positive x-direction, the nanoDSF and backreflection measurements can be performed, in which all capillaries are scanned without stopping the sample carrier. When the sample carrier is retracted, i.e. moved in negative x-direction, the respective DLS measurement can be performed, during which the sample carrier stops for the respective measurement. In case not all capillaries placed in a sample holder shall be measured, a subset of capillaries can be selected which are then considered as the optics can detect the scattering intensity of a respective sample comprised in a capillary.

Figure 10:
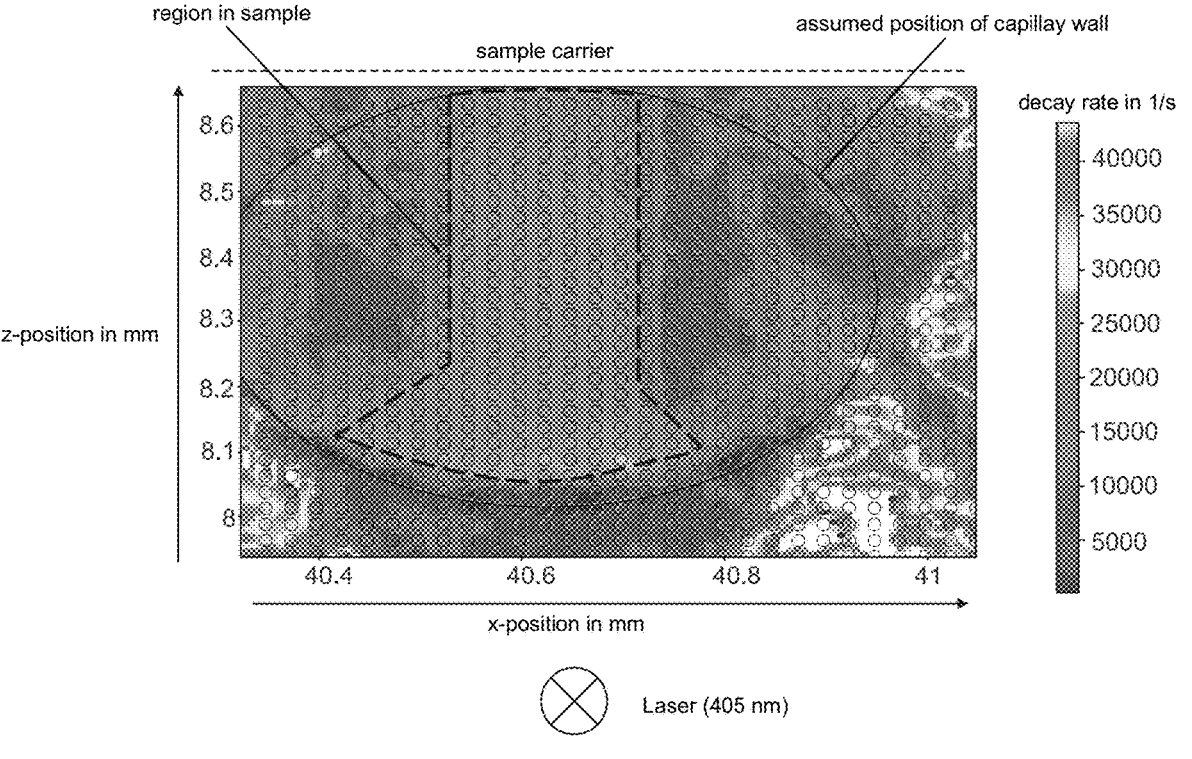
FIG. 10: Representation of the decay rate (inversely proportional to the particle radius) as a function of the measurement position. The white circles symbolize the analyzed measurement positions.

For the respective measurement the positioning of the vessel is crucial in order to obtain high quality results. Moreover, also the determination of the measurement spot within the vessel can enhance the quality and sensitivity of the measurement. As mentioned above, measuring the position of the vessel can be achieved by different methods, wherein using the autofluorescence signal from the particles and/or the vessel is preferred. A preferred method is explained in further detail with reference to FIG. 10. For determining the thermal stability of a particle such as a protein in solution for example, the sample comprising the protein in solution can be heated from 20° C. to 95° C. ("temperature ramp"). Especially in case more than one vessel comprising a sample is to be analyzed, said samples may be positioned for example in a sample holder on a sample deck that can be moved per measurement cycle, i.e measurement at each of at least one predetermined temperature of the temperature ramp, so that all samples can be measured. Due to a temperature-induced expansion of the sample holder during such a temperature ramp, the positions of the vessels comprising the samples can shift slightly. The center of the vessel in x-direction is therefore preferably determined and optionally (re-)positioned for a measurement and/or each measurement cycle (such as a DSL and/or nano-DSF measurement) based on a fluorescence signal, e.g., the maximum of the fluorescence signal detected and/or of the previous fluorescence measurement. However, the measuring positions of a vessel, preferably a capillary, can differ from measurement to measurement due to measurement inaccuracies and/or weakly fluorescent samples. The z-position, on the other hand, is preferably set before a measurement and typically only changes by about ±20 μm during a temperature ramp from 20° C. to 90° C. due to expansion of the sample holder. If the measuring position in the x-direction deviates more than a predetermined value from the center of the vessel, the measurement might be influenced by the scattering signal of the vessel wall. In addition, the light might be refracted differently by the curvature of the vessel wall depending on the measuring position, so that deviating measuring positions can influence the measuring angle and thus the particle characteristic, e.g. the decay rate of the particle, to be determined. The decay rate of the sample can therefore be determined correctly at certain measuring points within the vessel, the so-called "measurable area of the vessel" (indicated in the FIG. 10 as a green area; white circles symbolize the analyzed measurement positions). This area depends on the correct focusing of the sample. Different decay rates can be observed for the same sample if the light is so strongly refracted by the curvature of the vessel wall that the detector can no longer detect the illuminated area. The autocorrelation function(s) recorded in such a case would contain primarily interference signals (e.g. ambient light or electronic noise). In addition, the capillary wall at the top of the capillary can have a strong influence on the scatter signal (violet spots at low z-values), which may lead to artefacts resulting in meaningless data. Thus, as shown in FIG. 10, a z-position in the upper part of the vessel (low z-values) is best for obtaining accurate results. Thus, using a fluorescence scan is advantageous for precisely locating and optionally (re-)positioning a vessel for obtaining reproducible and accurate measurement results.

In addition to the determination, it is further preferred to find the best spot inside the vessel, i.e., the spot within the vessel where the best signal to ratio can be obtained.

For instance, a measuring spot next to a wall of the vessel may enhance the noise. For instance, using a preferred capillary has an inner diameter of 500 μm, but the size (e.g. diameter) of the best spot for measuring is preferably only ~50 μm. With the autoflorescence measurement and the use of the strong focusing lens, an 10 μm precision is achieved.

The preferred spot with the best signal to noise ratio (SNR) can be found by performing multiple DLS measurements at different positions inside the capillary, e.g. using a weakly scattering sample. The most preferred spot is preferably the spot with the highest SNR of the autocorrelation function (SNR=(amplitude of acf)/(sum of squared fit residuals)). For example, with a 2 mg/ml Lysozyme containing solution, a typical value for the SNR=50 is obtainable with a measurement duration of 200 ms. As example a typical value of the SNR is 50 when using lysozyme In preferred embodiments, the method according to the present invention comprises the steps of i) providing a vessel comprising a sample of particles in solution under study; ii) transmitting light from a first provided light source to the vessel; measuring fluorescence emitted from the vessel and or the sample comprised therein; determining the position of the vessel relative to the first optic comprising the first light source based on the detected, emitted light; determining the position of the measurable area of said vessel relative to said first optic based on the detected, emitted light; optionally (re-) positioning the vessel relative to the first optic; and performing a fluorescence measurement, in case the information, e.g. signal intensity, obtained from the detected, emitted light indicates the presence of particles under study; iii) transmitting light from a second provided light source to the vessel; and performing a DLS measurement, in case the information, e.g. signal intensity, obtained in step ii) from the detected, emitted light indicates the presence of particles under study; and iv) determining characteristics of particles in solution under study, such as particle size distribution and/or presence and/or amount of aggregation, based on information obtained from the performed fluorescence and DLS measurements in steps ii) and iii). The method may further comprise, e.g. before step ii), a step iv) of tempering the vessel. Further, the step of measuring fluorescence preferably refers to a step of measuring autofluorescence by performing a nano-DSF measurement. Furthermore, the method can be performed repeatedly by iteratively performing steps ii) and iii), and/or steps iv), ii) and iii). Alternatively or additionally, a step of measuring back-reflection and/or static light scattering, e.g. using the first optic, may further be comprised in the method according to the present invention. Of note, the first and the second optic can be the same or different ones.

The present invention relates in a second aspect to a device for measuring characteristics of particles in solution, wherein said characteristics of particles in solution are preferably measured in accordance with the method according to the present invention described above. Thus, the device according to the present invention is preferably used for performing the method according to the present invention and/or the method according to the present invention is preferably performed using the device of the present invention.

The device according to the present invention comprises means for accommodating at least one vessel comprising a sample of said particles in solution, preferably for accommodating between 0.1 to 15 μL of said particles, more preferably between 1 μl and 15 μl, and even more preferably between 8 μL and 12 μL. Said means can comprise for example a sample holder such as a capillary holder or a microwell plate holder.

The device according to the present invention further comprises a monochromatic light source, preferably a laser, and a light detector, preferably a PMT, a SiPM, or an APD photon counting detector.

The device according to the present invention further comprises means for performing a DLS measurement. Said means may comprise for example an FPGA, a pulse discriminator, a correlator, an ADC, and a lens such as a collimating lens and/or an objective lens (or an objective mirror).

Figure 6A:
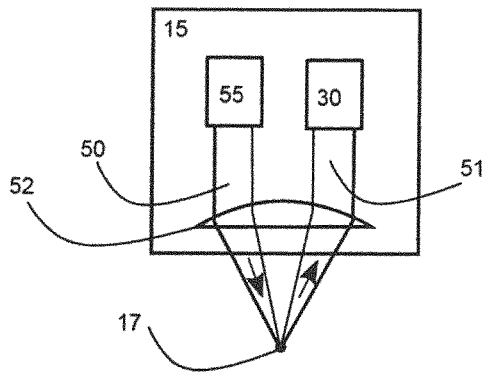
FIG. 6: A) Scheme of a DLS optics. B) A part of a CAD model (sectional view) of a DLS optics with two collimator lenses.
Figure 6B:
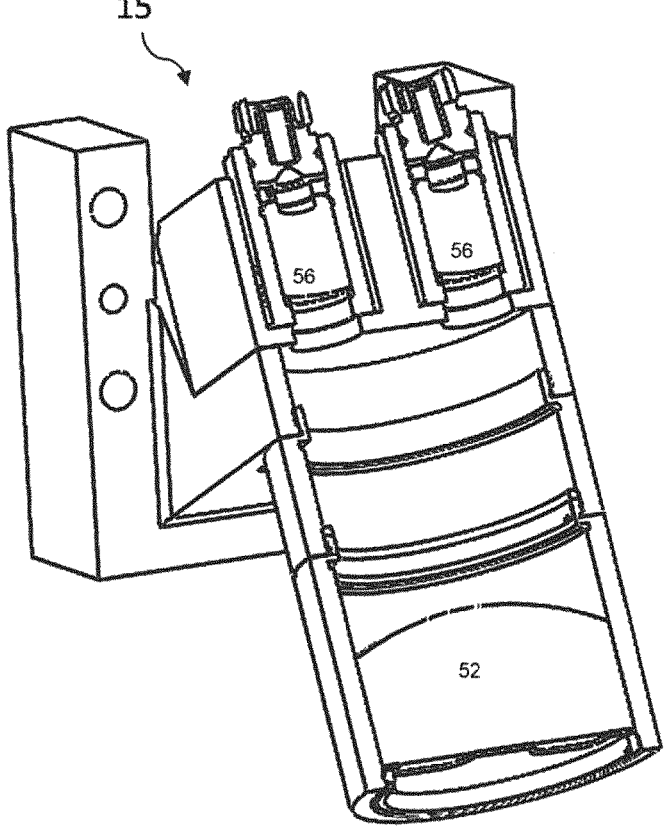
Figure 7A:
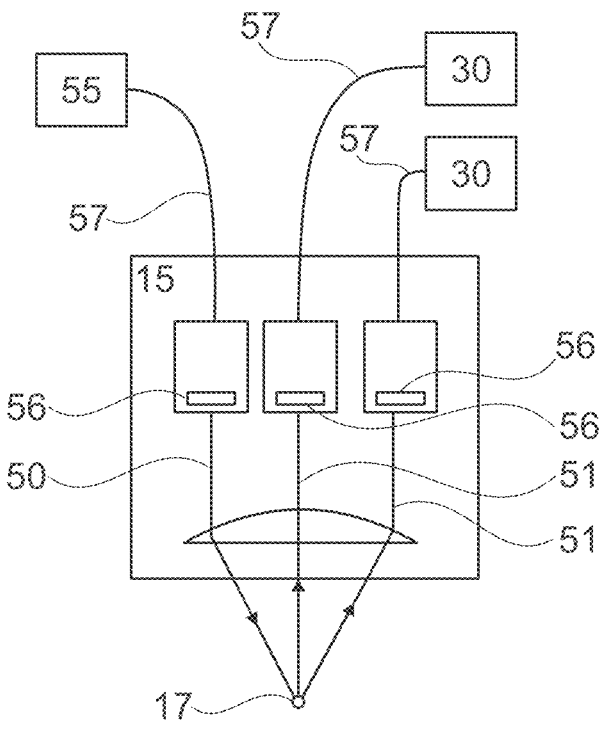
FIG. 7: A) Scheme of a DLS optics with one excitation and two detectors, e.g. a photodiode with multimode fiber and a PMT with single mode fiber. B) Confocal version of a DLS optics. C) Combined fluorescence optics and DLS optics confocal (x-distance=0). D) Design of a DLS optics with free space coupled light source. E) Design of a DLS optics with lens hood, astigmatism correction, fluorescence blocking filter and polarization filter. F) Design of a DLS optics with two DLS arms and one confocal fluorescence optic for simultaneous measurement at one point. G) Design of a DLS optics with two arms without objective lens.
Figure 7B:
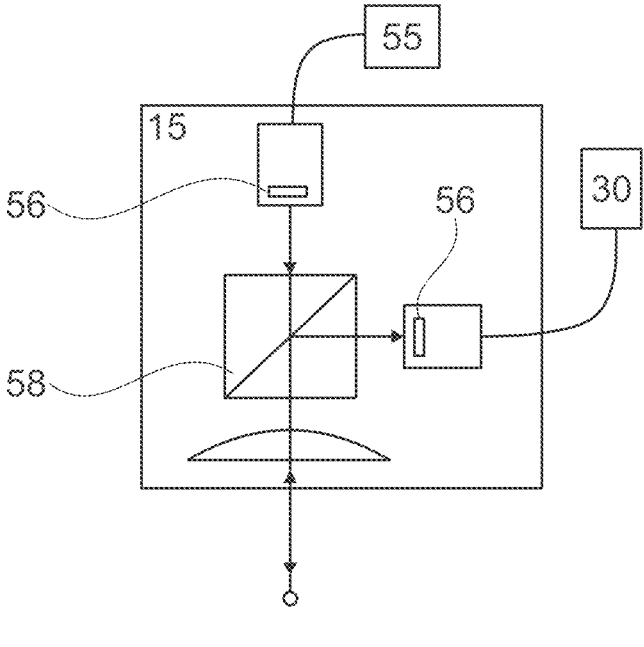
Figure 7C:
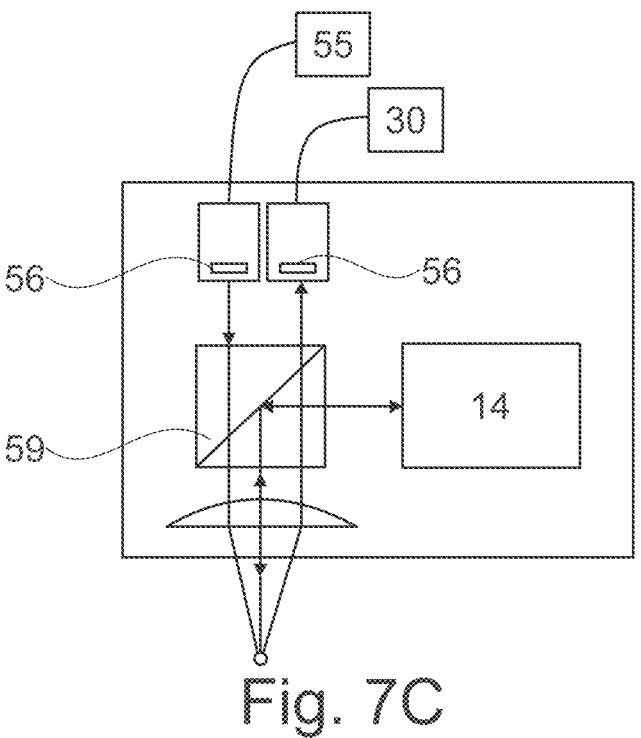
Figure 7D:
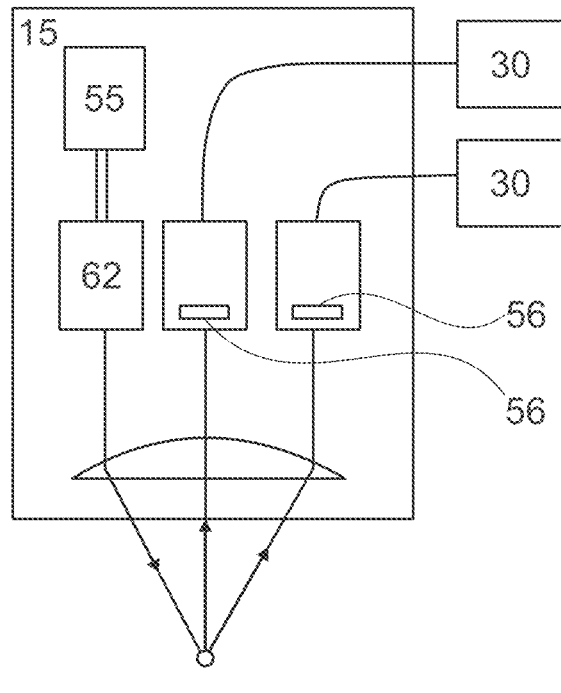
Figure 7E:
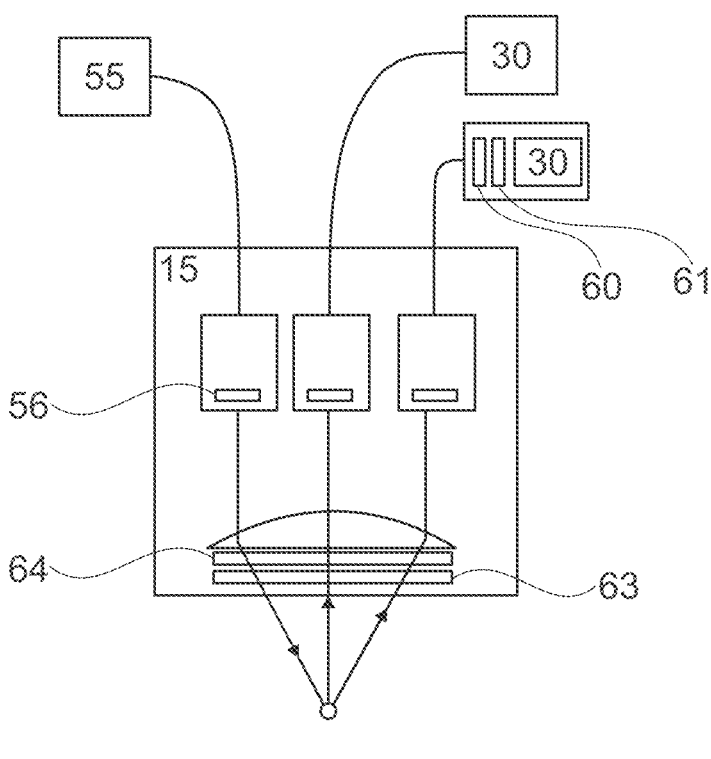
Figure 7F:
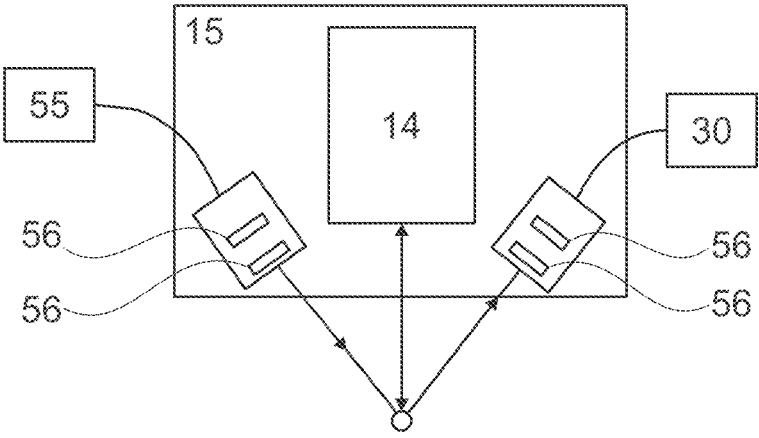
Figure 7G:
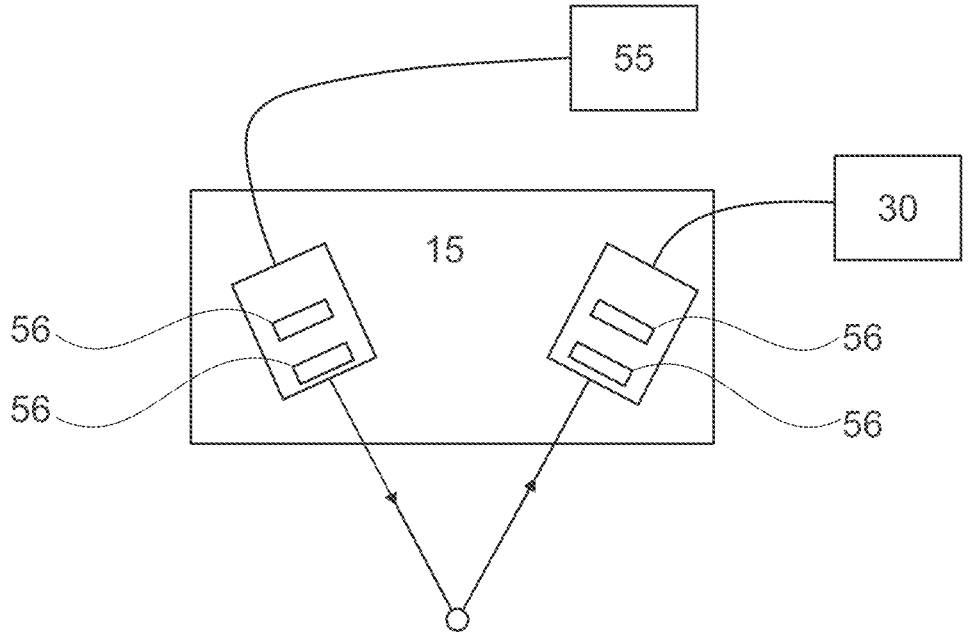
Figure 8A:
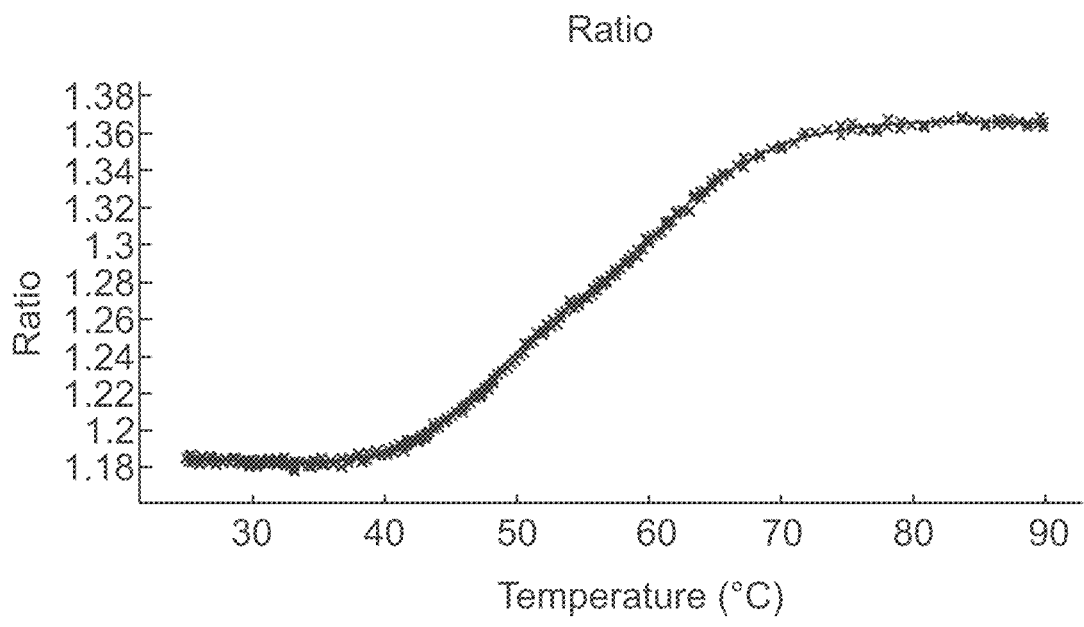
FIG. 8: A) Combined measurement of fluorescence shift and particle size distribution over temperature of IgG in sodium acetate buffer. B) Combined measurement of fluorescence shift and mean particle size over temperature from IgG in sodium acetate buffer. C) Combined measurement of fluorescence shift and particle size distribution over temperature of IgG in HEPES buffer. D) Combined measurement of fluorescence shift and mean particle size over temperature of IgG in HEPES buffer.
Figure 8B:
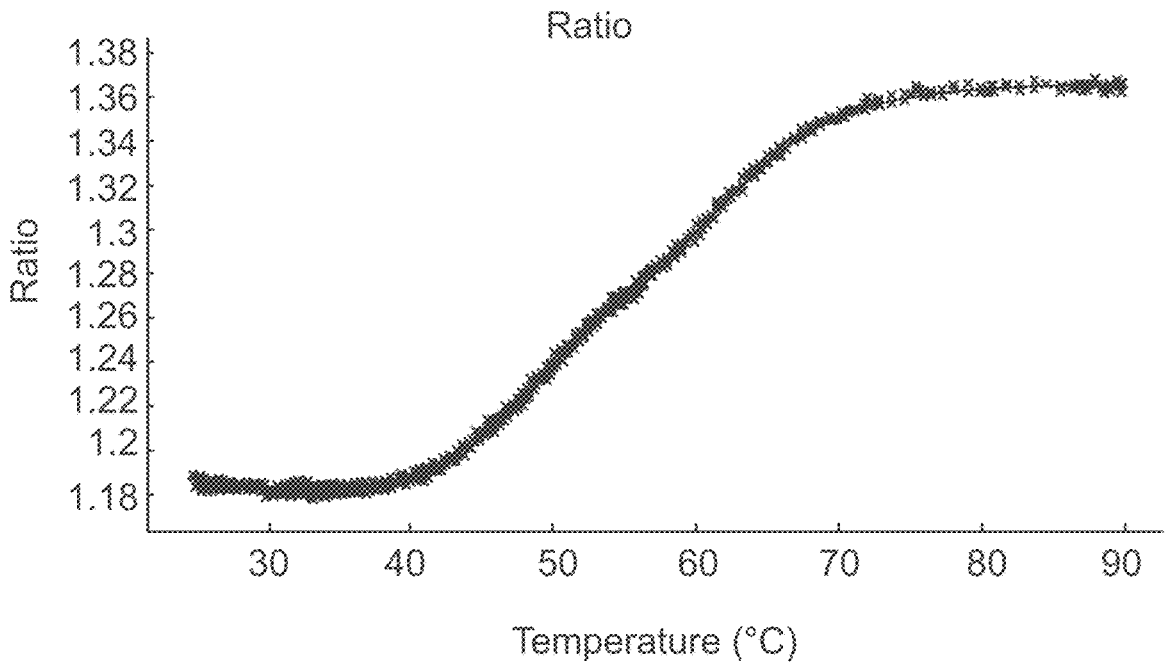
Figure 8B:
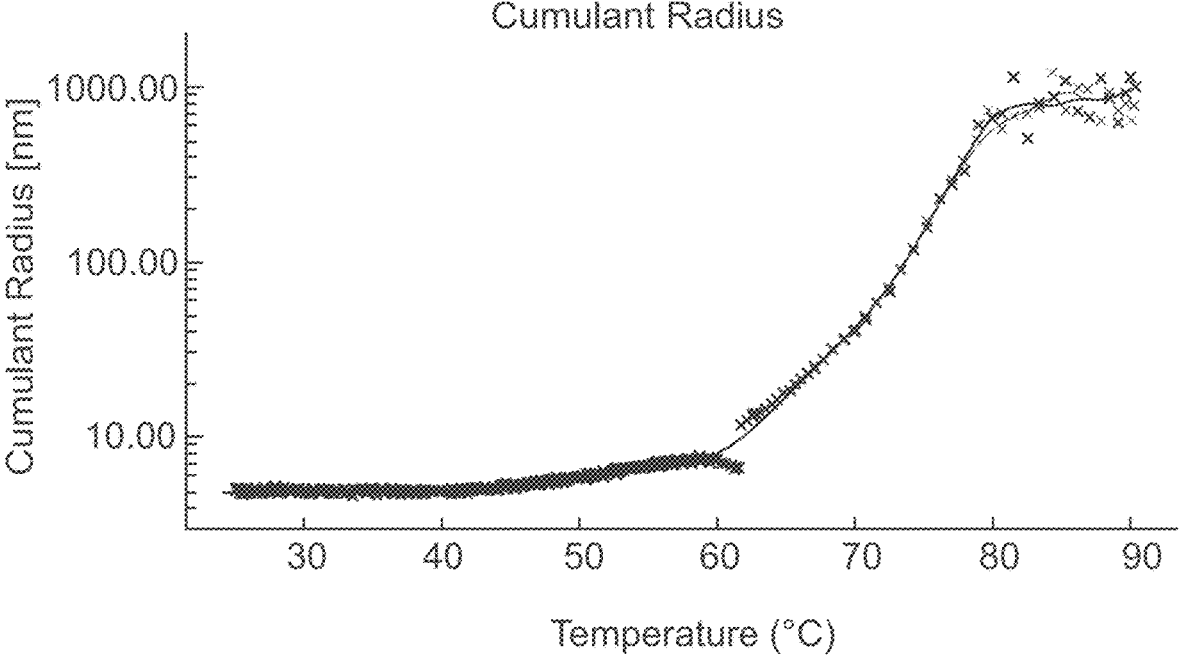
Figure 8C:
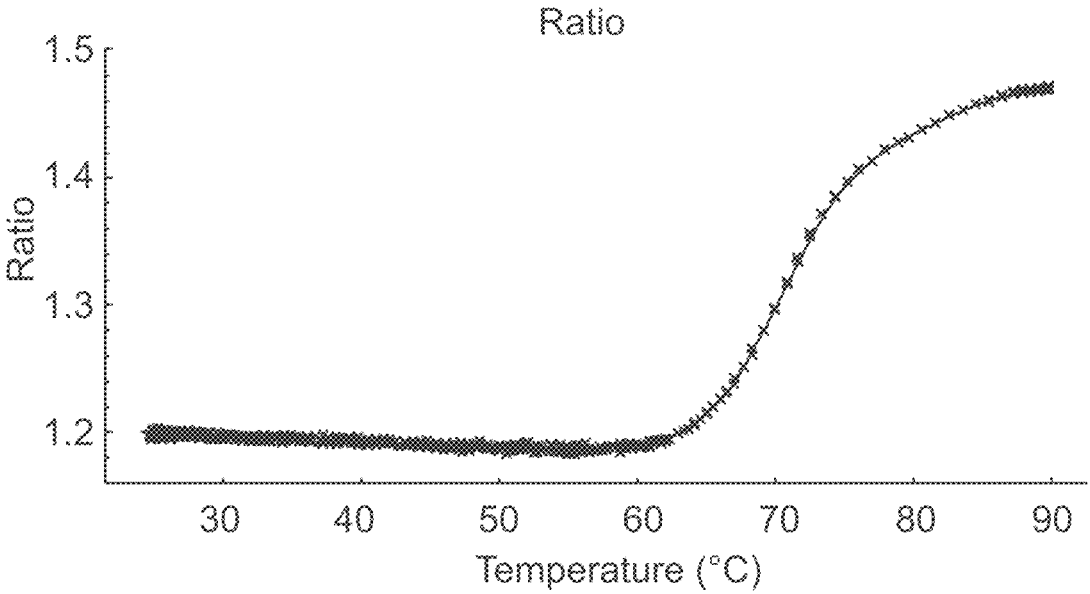
Figure 8C:
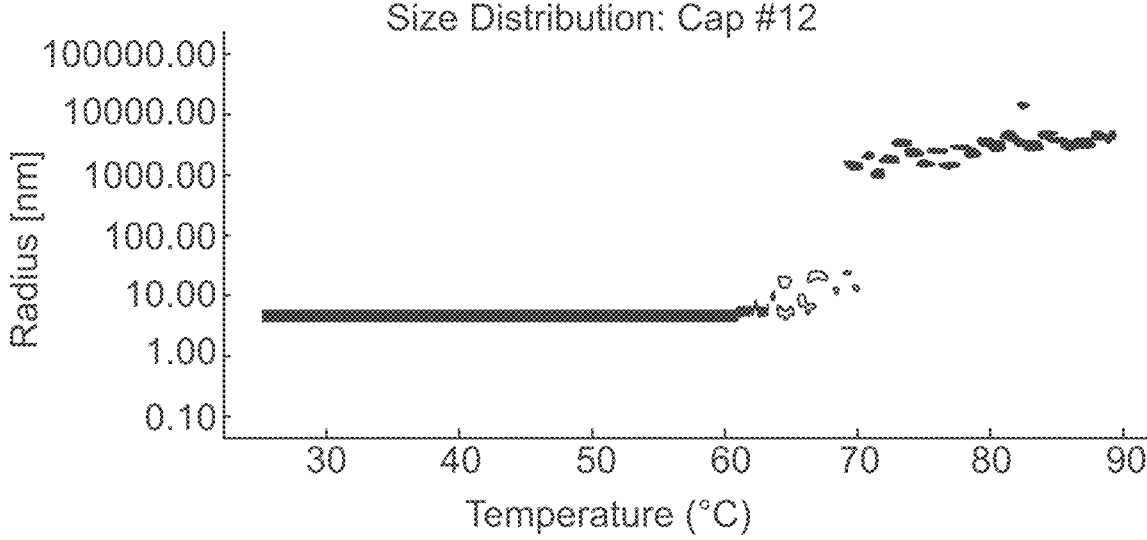
Figure 8D:
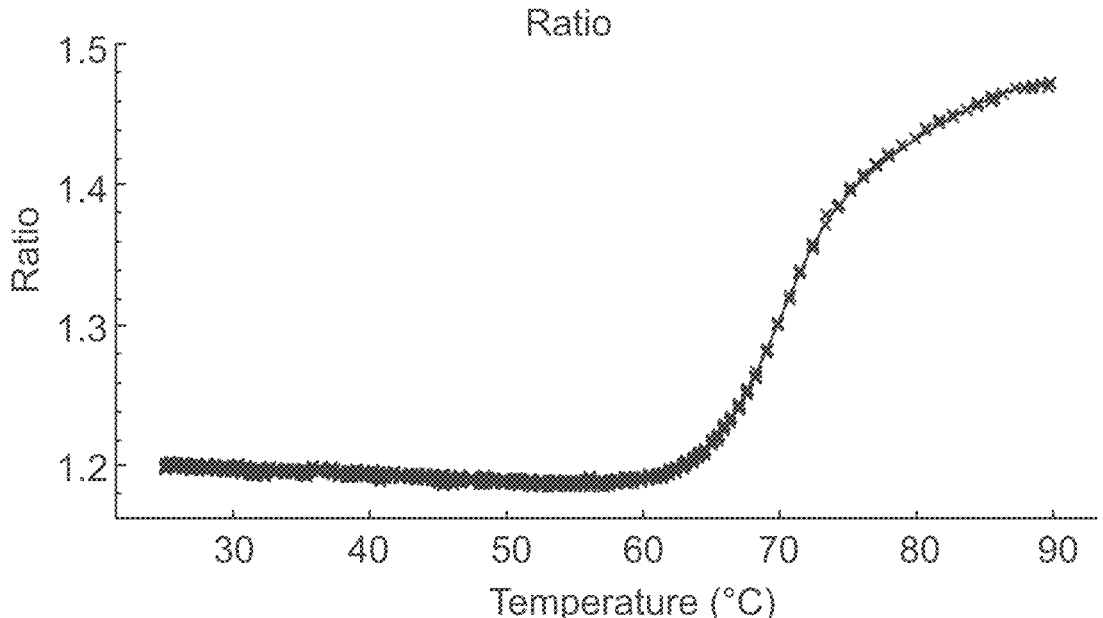
Figure 8D:
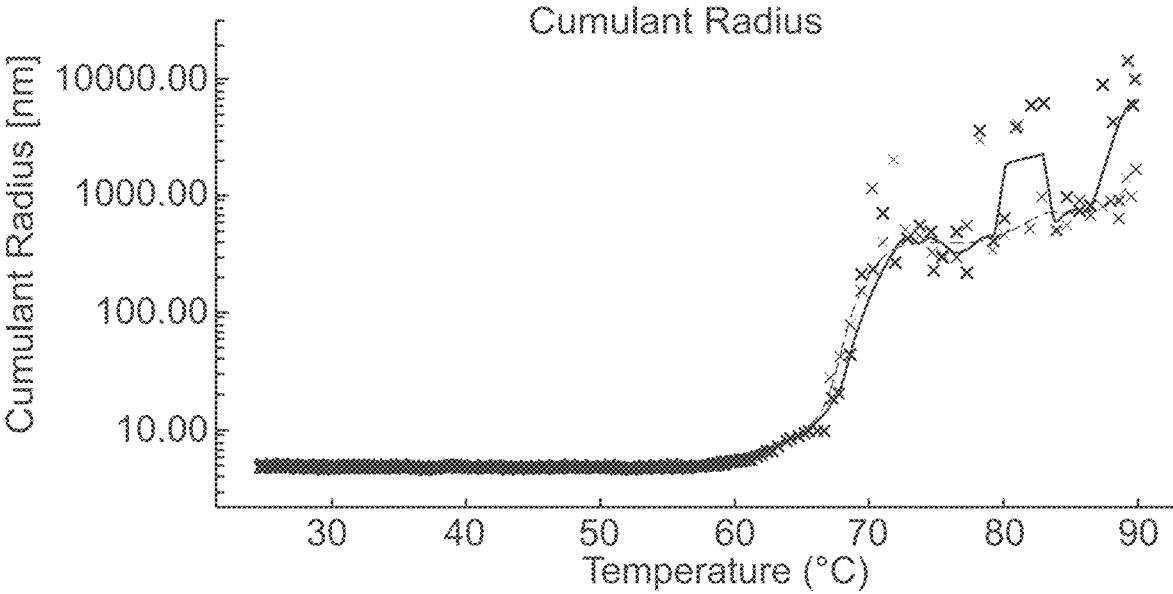

Means of the device according to the present invention, such as means for performing a DLS measurement, may be comprised in a DLS optics. Said DLS optics may further comprise a monochromatic light source, a light detector, and/or a part or all of the control means. Thus, the device may comprise a DLS optics as exemplarily depicted in FIG. 6. A DLS optics 15 comprises a monochromatic light source 55, e.g. a laser, a DLS detector 30, and preferably an objective lens or an objective mirror 52 as shown in FIG. 6 A). Thus, an excitation beam 50 can be provided by the monochromatic light source 55 that can be focused by the objective lens 52, preferably such that the resulting fluorescence focus 17 is located within a sample under study. In case a sample is analyzed using the device and the method according to the present invention, particles in solution comprised in the sample scatter the light transmitted from the DLS optics 15. The thus obtained emitted light/scattered light can be detected 51 by the DLS detector 50. In particular, the detected light beam 51 can be focused and localized by the same or another objective lens (or objective mirror) 52 comprised in the DLS optics 15 such that it can be detected by a DLS detector 30 such as a PMT or a SiPM. A part of a CAD model (sectional view) of a DLS optics 15 is exemplarily shown in FIG. 6 B), wherein the DLS optics 15 comprises two collimator lenses 56 and an objective lens 52. A collimator lens 56 can be used to generate light with an approximately parallel beam path from a divergent light source such as scattered or emitted light from a sample under study. A collimator lens is also advantageous for the excitation light beam from a monochromatic light source 55 (not shown) being focused by the objective lens 52 and/or a detected light beam for detection by the DLS detector 30 (not shown).

The device according to the present invention further comprises control means adapted for controlling the means for accommodating at least one vessel, controlling the monochromatic light source for transmitting light from the monochromatic light source to the at least one vessel, controlling the light detector for detecting signals from the at least one vessel, and controlling said means for performing a DLS measurement.

Preferably, the device according to the present invention further comprises means for performing a correlation operation, preferably an autocorrelation operation. Moreover, said autocorrelation operation is preferably an autocorrelation logic embodied in hardware and/or software.

Preferably, the device according to the present invention further comprises means for performing a data processing operation. Said data processing operation preferably comprises a data processing logic at least for performing the step(s) of processing the obtained analog output signal of the method according to the present invention as described above. Moreover, said data processing operation is preferably a data processing logic embodied in hardware and/or software.

Preferably, the device according to the present invention further comprises means for digitalizing signals obtained from the light detector, wherein the control means are adapted for controlling said means for digitalizing signals obtained from the light detector. Said means for digitalizing signals obtained from the light detector comprise preferably a field programmable gate array (FPGA).

Preferably, the device according to the present invention further comprises a single mode fiber, and means for transmitting monochromatic light from the monochromatic light source via said single mode fiber, wherein the control means are further adapted for controlling said means for delivering monochromatic light from the monochromatic light source via said single mode fiber.

Thus, the device may comprise a DLS optics and an optical fiber, preferably a single mode fiber, a polarization-preserving or a multi-mode fiber, more preferably a single mode fiber. As exemplarily depicted in FIG. 7 A), a monochromatic light source 55, e.g. a laser, is not located directly in the depicted DLS optics 15 in contrast to the DLS optics exemplarily depicted in FIG. 6 A) described above, though connected to it via an optical fiber 57 which delivers monochromatic light from the monochromatic light source 55 to a collimating lens 56 located in the DLS optics 15. The DLS optics 15 comprises one or more, here two, further collimating lenses 56 each for focusing a detected light beam 51 that is transferred via a further optical fiber 57 to a light detector (not directly located in the DLS optic in this example; 30). Thus, FIG. 7 A) depicts exemplary a scheme of a DLS optics with one excitation and two light detectors, e.g. a photodiode with multimode fiber and a PMT with single mode fiber.

Another example of a device is exemplarily shown in FIG. 7 B) showing a confocal version of a DLS optics. Compared to FIG. 7 A) described above, the DLS optics 15 comprises further a beam splitter 58 for splitting a light beam for example with equal ratio in two light beams which can be focused by a collimator lens 56 each. This has the advantage that less space is needed.

Preferably, the device according to the present invention further comprises means for measuring the fluorescence of said particles in solution comprised in the sample, wherein the control means are further adapted for controlling said means for measuring the fluorescence of said particles in solution comprised in the sample.

Thus, a further example of a device is exemplarily shown in FIG. 7 C) depicting a combined fluorescence optics and DLS optics confocal (x-distance=0). Compared to FIG. 7 B) described above, the DLS optics comprises the fluorescence optics 14 and the beam splitter 58 has a predetermined beam splitter wavelength 59, e.g. low pass 620 nm. Thus, the detected light beam 51 is split into two light beams, wherein only light with a wavelength of 620 nm or less is passed to the fluorescence optics 14. Such a setup has the advantage that less space is required, and that fluorescence and scattering can be measured simultaneously and using the same sample.

Preferably, the device according to the present invention further comprises positioning means for positioning the means for accommodating the sample of said particles in solution, wherein the control means are further adapted for controlling the positioning means for accommodating the sample.

Preferably, the device according to the present invention further comprises a temperature control system for tempering the vessel over time at least with a first temperature at a first time point and a second temperature at a second time point, wherein the control means are further adapted for controlling said temperature control system for tempering the vessel over time at least with a first temperature at a first time point and a second temperature at a second time point.

Preferably, the device according to the present invention further comprises means for performing a nano-DSF measurement and/or means for measuring back-reflection, wherein the control means are further adapted for controlling said means for performing a nano-DSF measurement and/or said means for measuring back-reflection.

Preferably, the device according to the present invention further comprises a further light detector; and means for performing a static scattering light measurement, wherein the control means are further adapted for controlling said means for performing a static scattering light measurement.

The device according to the present invention can further comprise means for improve the beam quality of the laser.

Hence, a device according to the invention can comprise an optics to improve the beam quality of the laser, for example comprised in the DLS optics.

As another example of a device according to the present invention, a device is exemplarily shown in FIG. 7 D), wherein in contrast to the device depicted FIG. 7 A) described above, the laser is coupled without single-mode fiber. This has the advantage of reducing costs and power loss when coupling into the fiber. In the example depicted in FIG. 7 D), the monochromatic light source is for example located in the DLS optics 15. Thus, exemplarily shown in a design of a DLS optics with free-space coupled light source is depicted.

The device according to the present invention can comprise further means that are advantageous for improving the quality of the measurement such as a dichroic filter, a polarization filter, an aperture to reduce stray light, and/or a cylindrical lens for correction of capillary astigmatism. Thus, another example of a device is exemplarily shown in FIG. 7 E), wherein a cylindrical lens for correction of capillary astigmatism 64 is positioned between an aperture to reduce stray light 63 and the objective lens 52. Thus, a light beam transmitted from the monochromatic light source 55 can pass a collimating lens 56, then the objective lens 52, the cylindrical lens 64, and then the aperture 63 before being scattered by a sample for example. The scattered light can then be detected by a light detector 30 upon passing the DLS optics 15 and in particular, the aperture 63, the cylindrical lens 64, the objective lens 52, and then at least one further, e.g. two, collimating lens 56. As furthermore exemplarily shown in FIG. 7 E), the light detector 30 such as a DLS detector can comprise a dichroic filter 60, e.g. with bandpass 405/5 nm to block fluorescence, and/or a polarization filter 61. This is especially advantageous for weakly scattering samples that show autofluorescence (band pass) or particles with a high aspect ratio (polarization filter).

A further example of a device is depicted in FIG. 7 F), showing a design of a DLS optics with two DLS arms (detection and excitation) and one confocal fluorescence optic for simultaneous measurement at one point. In this design, the DLS optics 15 comprises a fluorescence optics 14 as well as collimating lenses 56, for example two collimating lenses 56 in series without objective lens for transmitting light from the monochromatic light source 55 to a sample and for transmitting emitted light from the sample to the light detector (3), respectively. In this design, the, in direction of the respective light beam passing said two collimating lenses 56 in series, second collimating lens 56 focuses the excitation. Such a design of a DLS optics is advantageous as of larger scattering angles, i.e. angles between laser and detector, can be achieved in this way, and it may also allow a reduction of light scattering.

Figure 5:
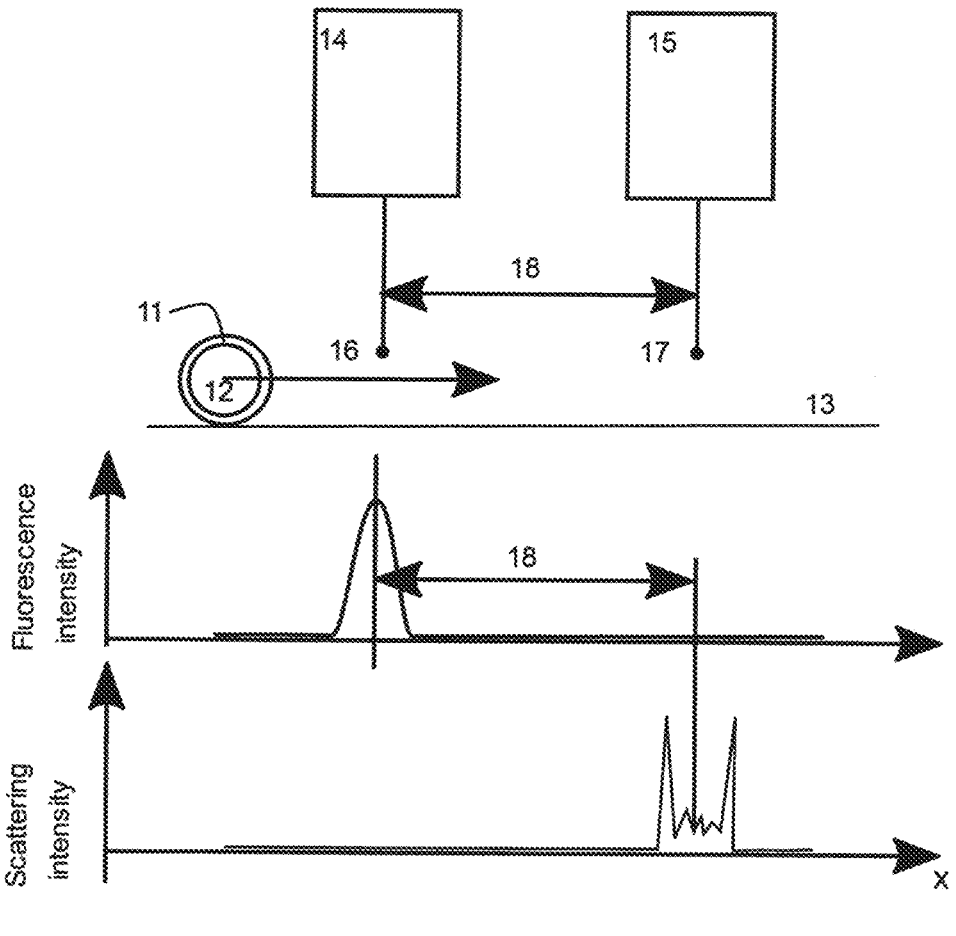
FIG. 5: Scheme of a measuring system according to the present invention.

A further, preferred, example of a device is depicted in FIG. 7 G), showing a design of a DLS optics with two arms (detection and excitation) without objective lens as in case of FIG. 5 F), though without fluorescence optics 14. This is especially advantageous as fluorescence and scattering measurements can thus be obtained simultaneously for the same sample.

As regards the vessel, the sample, the particles and their characteristics, the sample, the vessel, the monochromatic light source, the light detector, the tempering over time, the (auto)correlation operation, the FPGA, as well as the delivery, transmission, emission, and detection of light, and the measurements, including DLS measurement, fluorescence measurement, nano-DSF measurement, back reflection measurement, and static scattering light measurement, the same applies as described above in connection with the method according to the present invention. Moreover, also the other features of such a measurement can be as described above. Hence, advantageous features and characteristics of the first aspect of the present invention are to be regarded as advantageous features of the second aspect of the present invention and vice versa.

Other aspects and advantages of the present invention will be described in the following examples, which are given for purposes of illustration and not by way of limitation. Each publication, patent, patent application or other document cited in this application is hereby incorporated by reference in its entirety.

Examples

Methods and materials are described herein for use in the present disclosure; other, suitable methods and materials known in the art can also be used. The materials, methods, and examples are illustrative only and not intended to be limiting.

The immune system can recognize and fend off pathogens (e.g. bacteria, viruses, toxins) either by a humoral and/or a cell-mediated immune response. The humoral immune response involves the production of specific proteins, including pathogen-specific antibodies that are directed against pathogen-specific antigens. Antibodies can circulate as soluble proteins in the blood plasma and lymphatic fluid and are of relevance for the recognition, neutralization, agglutination and precipitation of pathogenic antigens. Due to their specificity against pathogenic antigens as well as their fundamental role in the context of immunity in general leads, antibodies are of high relevance in the fields of diagnosis and treatment of diseases.

However, investigating antibodies and developing antibody-based therapies and pharmaceutical compositions are complex tasks in terms of the function and stability of antibodies. For example, instability of antibodies can be caused by chemical modification, change—especially decrease—of the thermal stability of their conformation, and change—especially decrease—of their colloidal stability. Any of these aspects can affect the efficiency and/or safety of a therapeutic and/or diagnostic antibody. Thus, extensive analyses are performed aiming at comprehensively characterizing and optimizing the stability of antibodies.

In this context, an experiment was performed in order to simulate a typical experiment to analyze and optimize the stability of a protein in solution, e.g. a (pharmaceutical or diagnostic) antibody composition comprising IgG and a buffer.

The starting material was a commercially available preparation (HyQvia, Baxalta Innovations GmbH, Vienna, Austria) of a therapeutic antibody of immunoglobulin class G (abbreviation: IgG). IgG antibodies were diluted using different buffers (sodium acetate and HEPES). The initial mass concentration of the HyQvia product was 100 mg protein per 1 ml injection solution. The antibody composition was diluted 50-fold using the sodium acetate or HEPES buffer to a final mass concentration of 2 mg protein per 1 ml buffer. Diluted preparations were centrifuged for 15 minutes at 14000-fold acceleration due to gravity to remove insoluble macro- and microscopic particles. Capillaries were loaded with the diluted and centrifuged antibody solution by holding one capillary each in the protein solution, which filled itself with protein solution by capillary forces. A combined thermal deconvolution experiment consisting of almost simultaneous measurements of fluorescence shift and particle size was performed. The heating rate to induce the thermal deconvolution was 1° C./minute. The DLS measuring time was 500 ms per capillary.

FIG. 8 shows results of the experiment that aimed at determining at which temperature IgG shows a fluorescence shift (always upper subplot) and how the distribution of the detected particles or their size (always lower subplot) changes as a function of temperature. The combinatorial determination of the stability of the protein conformation (always upper subplot) and the colloidal stability of the protein particles by measuring the size or size distribution (always lower subplot) in the protein solution allows a precise analysis of these two critical parameters. Since the combinatorial determination can also be performed on up to 48 samples in parallel, many different conditions, such as different buffers in which the protein under study is dissolved, can be tested and efficiently evaluated. Thus, a combination of DLS and nano-DSF measurement has the advantage of accelerating the development of diagnostic or therapeutic proteins by a combined characterization of the proteins in view of their protein conformation and their colloidal stability.

Figure 9:
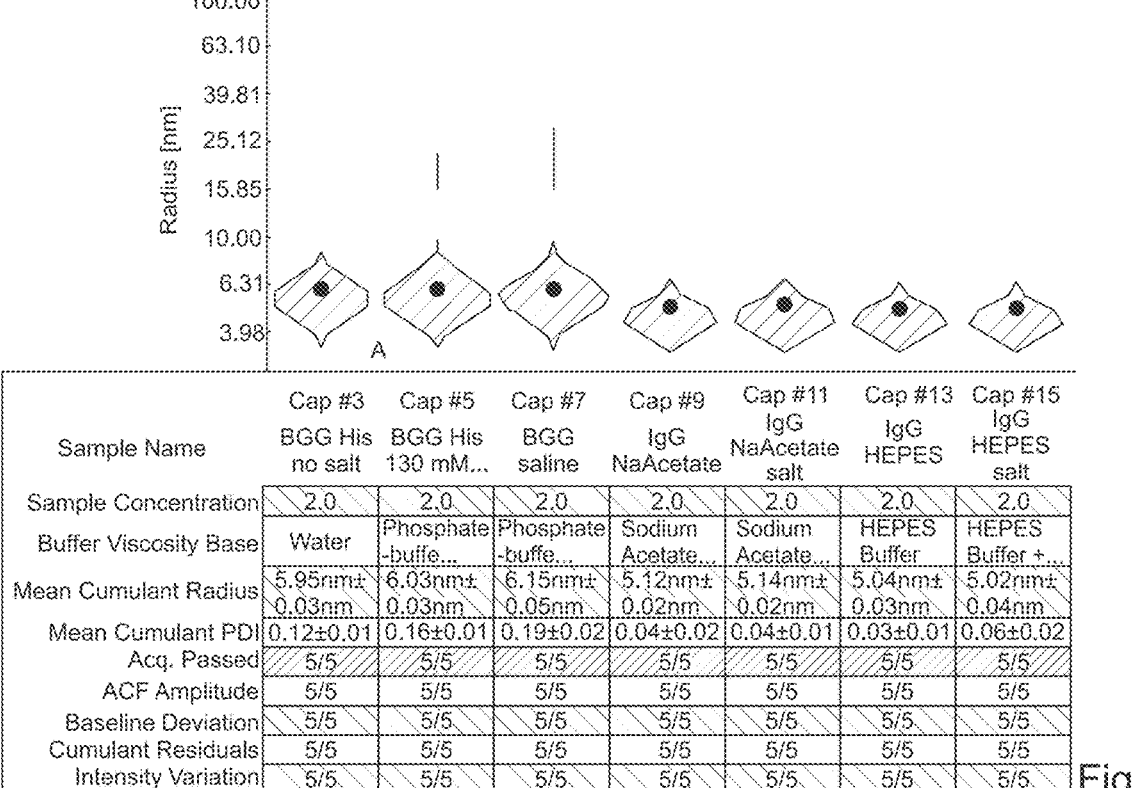
FIG. 9: Exemplarily summary of DLS quality parameters of different samples.

FIG. 9 shows an overview of DLS-determinable particle parameters, including average cumulative radius, average cumulative polydispersity index, and mathematical parameters of the autocorrelation function underlying the particle parameters. Data of a total sample, bovine globulin (BGG) and IgG from the buffers described in FIG. 8 are shown. The temperature was kept constant at 25° C. during the measurement. Five measurements, each with 5000 ms DLS measurement time, were recorded per capillary. The dots in the graph represent the average radius determined by the accumulator method. The grey areas represent the size distribution of the detected particles in the respective capillary. As it can be seen, differences between certain particle parameters of BGG and IgG could be identified. Such an experimental set up is advantageous for assessing the homogeneity of a given sample, e.g. the narrower the size distribution and the smaller the average cumulative polydispersity index, the more homogeneous is the sample under study.

Figure 15:
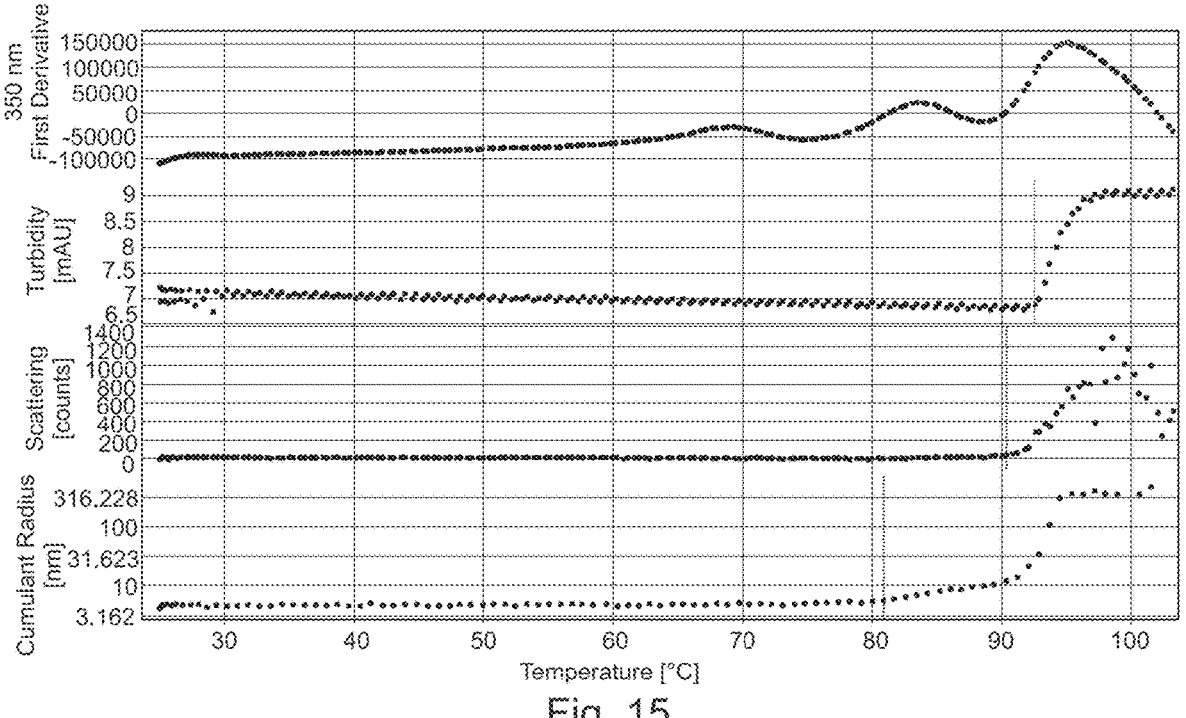
FIG. 15: Measurements of antibody buffer screen and antibody candidate selection.

FIG. 15 shows an application example for antibody buffer screen and antibody candidate selection by using NISTmAb reference material RM 8671, which is intended for use in evaluating the performance of methods for determining physicochemical and biophysical attributes of monoclonal antibodies. It also provides a representative test molecule for development of novel technology for therapeutic protein characterization.

The test sample comprises 1 mg/ml NISTmAb in Saline. The horizontal axis represents the temperature in a temperature range between approximately ambient temperature and more than 100° C. The first plot (from above) shows a first derivative at 350 nm over temperature. The peak between 60 and 75° C. indicates a first transition, the peak between 75 and 90° C. a second transition and the peak between 90 and 100° C. a third transition (better visible in this channel for this antibody). Each transition corresponds to unfolding of an individual protein domain. The second plot shows the turbidity from backscattering, wherein the onset is marked as straight vertical line. The third plot shows scattering from DLS (average scattering intensity), wherein the onset is again marked as straight line. The fourth plot (lowest plot) shows a cumulant radius in nm, wherein the onset is also marked as straight line.

IgG/antibodies (NIST mAb is representative) contain 3 protein domains: CH2, Fab fragment, CH3. In particular, the 'arms' of the Y-shaped IgG molecule contain the variable antigen binding sites and are therefore commonly referred to as the Fab region (fragment, antigen-binding). The 'foot' of the Y is responsible for the antibody's immunological properties and is called Fc region (fragment, crystallizable). The Fc region can be subdivided into the CH2 and CH3 domains (domains 2 and 3 of the constant parts of the heavy chains, respectively). In thermal unfolding experiments, three separate unfolding events are often visible in the unfolding profile, representing the three unfolding events of CH2 region, Fab region, and CH3 region. In particular, the CH2 region unfolds first (at the lowest temperature), followed by Fab and CH3. Depending on the exact molecular structure of the IgG, not all three regions may show as separate unfolding events. In some cases, two unfolding events may overlap or even occur simultaneously, precluding a clear separation. Unfolding of large Fab, which corresponds to the second transition, typically leads to size increase which is interpreted as cooperative unfolding (cumulant radius onset, lowest plot), but no aggregation. Unfolding of CH3, which corresponds to the third transition, causes aggregation visible in further size increase, but also from onsets in scattering (average intensity from DLS) and Turbidity (from back-reflection)

Figure 16:
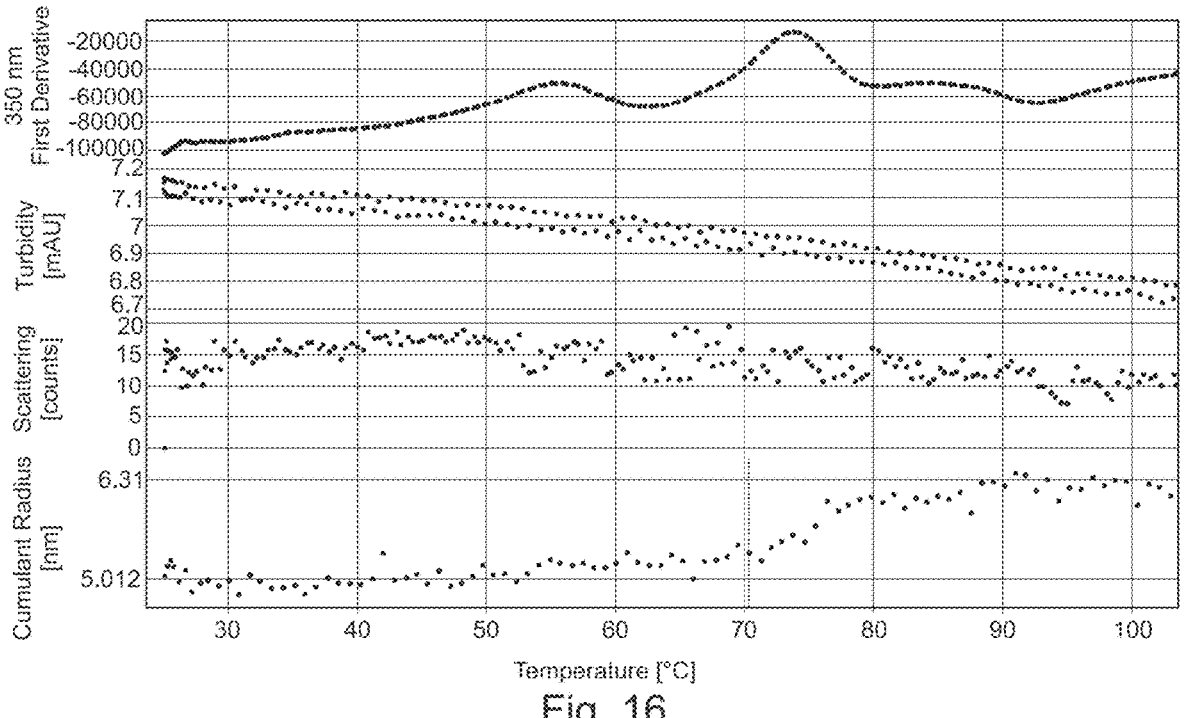
FIG. 16: Further measurements of antibody buffer screen and antibody candidate selection.

FIG. 16 is similar to FIG. 15, but the sample comprises 1 mg/ml NISTmAb in 25 mM sodium acetate pH4. The first plot (from above) shows a first derivative at 350 nm over temperature. The peak between 50 and 60° C. indicates a first transition and the peak between 70 and 80 a second transition (better visible in this channel for this antibody). Each transition corresponds to unfolding of an individual protein domain. The second plot shows the turbidity from backscattering. The third plot shows scattering from DLS (average scattering intensity). The fourth plot (lowest plot) shows a cumulant radius in nm, wherein the onset is marked as straight line. Unfolding of Fab leads to size increase, which is interpreted as cooperative unfolding. No aggregation occurs. In particular, this is a good example where the onset in DLS is not the onset of aggregation. So where aggregation is not observed, this onset should match the Tonset (for single domain proteins) but could be higher for multi-domain proteins and correspond to the unfolding of a domain resulting in the largest change of Rh. In this example, by monitoring DLS in combination with nDSF, one obtained more details about the unfolding mechanism of the protein.

Figure 17:
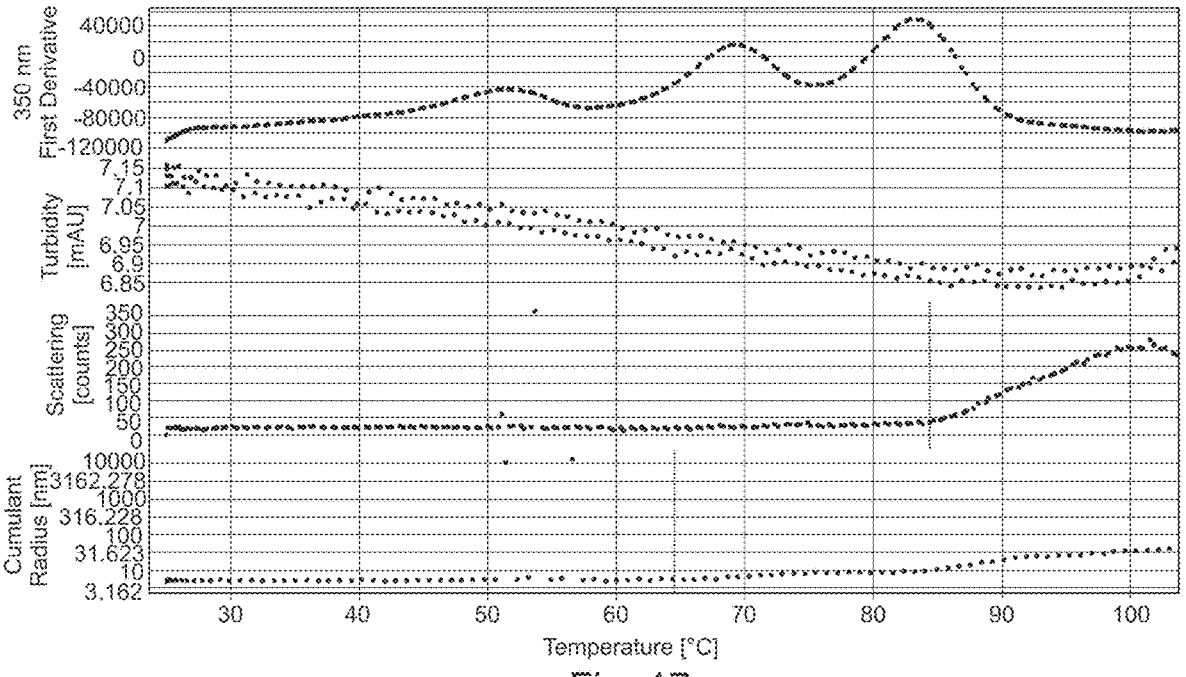
FIG. 17: Further measurements of antibody buffer screen and antibody candidate selection.

FIG. 17 is similar to FIG. 15, but the sample comprises 1 mg/ml NIST mAb in 25 mM sodium acetate pH 4+130 mM NaCl. The first plot (from above) shows a first derivative at 350 nm over temperature. The peak between 45 and 60° C. indicates a first transition, the peak between 60 and 75 a second transition, and the peak between 75 and 90° C. a third transition (better visible in this channel for this antibody). Each transition corresponds to unfolding of an individual protein domain. The second plot shows the turbidity from backscattering. The third plot shows scattering from DLS (average scattering intensity), wherein onset is marked as straight line. The fourth plot (lowest plot) shows a cumulant radius.

Unfolding of Fab, which corresponds to the second transition, leads to size increase, which is interpreted as cooperative unfolding. Unfolding of CH3, which corresponds to the third transition, causes mild aggregation which is visible as onset in scattering and the missing onset in turbidity.

These three examples show that corresponding results can be used to identify problematic domains of a candidate molecule and provide guidance on where to start with further optimization of constructs. Alternatively, these results can be used to identify promising buffer conditions.

Figure 18:
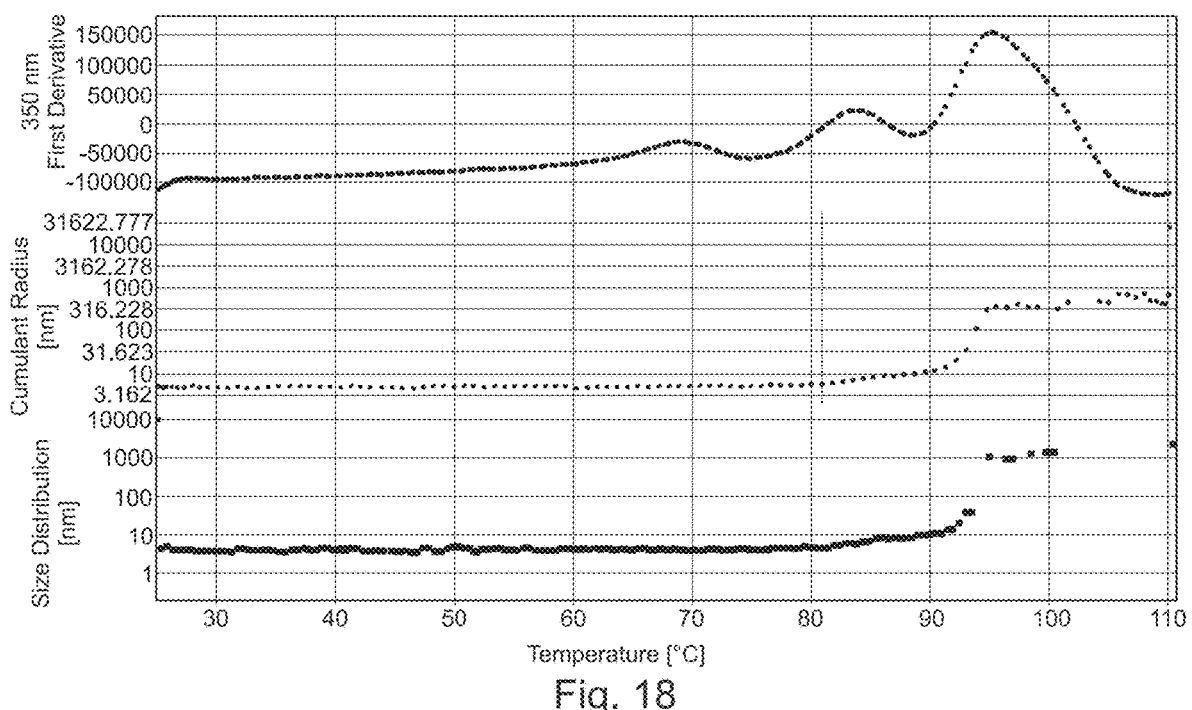
FIG. 18: Measurements for understanding aggregation pathways based on an example with random aggregation.
Figure 19:
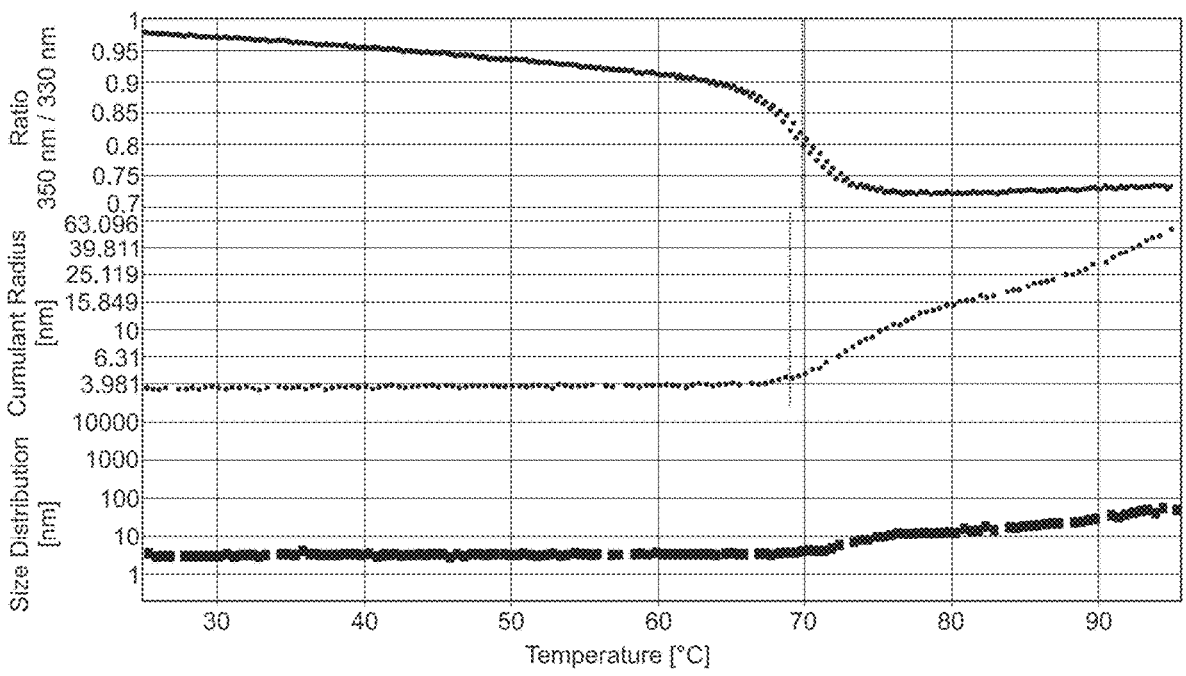
FIG. 19: Further measurements for understanding aggregation pathways based on an example with structured aggregation.

FIG. 18 is an example for understanding aggregation pathways. The sample is the same as in the example of FIG. 15 with a test sample comprising 1 mg/ml NISTmAb in Saline. It should be noted that upper temperature in FIG. 15 is above 100° C., whereas the upper temperature in FIG. 19 is about 110° C. Accordingly, the first plot (from above), which shows a first derivative at 350 nm over temperature, is to the first plot in FIG. 15. The second plot of FIG. 18 is also like the last plot of FIG. 15 which shows the cumulant radius. The third plot of FIG. 18 shows the size distribution over temperature. In this third plot, random aggregation is visible as speckle pattern upon unfolding of CH3 domain. Unfolding of Fab only results in size increase (onset in cumulant radius matches second transition in nanoDSF).

FIG. 18 is a further example for understanding aggregation pathways. The test sample comprises 2 mg/ml BSA (Pierce™ ampule (Bovine Serum Albumin Standard Ampules, Thermo Fisher Scientific, Rockford, United States)). From the there shown plots an aggregation in ordered fashion is derivable. In particular, in the second (middle plot), which shows ta cumulant radius, a steady increase in size distribution is visible upon unfolding, which is derivable from the first (upper) plot, showing a ratio signal. The second plot only shows the average size of all particles (the cumulant radius), while the third plot shows the size distribution (distribution of radii). In the third plot a steady increase in size is visible upon unfolding. In contrast to the speckle pattern in the size distribution of FIG. 18, a steady increase in the size distribution indicates aggregation in an ordered fashion Hence, combining fluorescence readout with DLS helps to understand aggregation pathways (random or structured aggregation). In a similar fashion it is possible to distinguish native from non-native aggregation by comparing unfolding transitions in the fluorescence signal to the size distribution over temperature. A speckle pattern prior to the transition midpoint would be indicative of aggregation from the native state.

Further preferred embodiments of the present invention are further specified in the following aspects.

1. Method to measure characteristics of particles in solution, said method comprising the steps of:

providing a vessel comprising a sample of said particles in solution, wherein the sample has preferably a volume between 0.1 μL and 15 μL;

providing a monochromatic light source and a light detector;

transmitting light from the monochromatic light source to the vessel comprising the sample;

detecting light emitted from the vessel with the light detector; and determining characteristics of said particles in solution comprised in the sample based on a dynamic light scattering (DLS) measurement.

For instance, it is preferred to provide the monochromatic light source for the DLS measurement. It is preferred to use a laser for the DLS measurement. It is further preferred to provide an additional light source for a fluorescence measurement. For instance, it is preferred to provide an LED which emits light at about 280 nm. It is still further preferred to provide an additional light source for a back-reflection measurement. For example, an LED which emits light at a wavelength of 385 nm may be used.

Depending on the provided light sources and the performed measurements it is preferred that a light detector is used for the DLS measurement. It is further preferred to provide an additional light detector for a back-refection measurement, preferably a detector for detecting the wavelength of the light source used for the back-reflection measurement, e.g., for detecting light at about 385 nm. It is still further preferred to provide at least one further, preferably two further light detectors for a fluorescence measurement(s). Preferably, the detected light for the fluorescence measurement comprises a longer wavelength than the light with is used for exciting fluorescence. For instance, one or two light detectors for detection of light at 330 nm and/or at 350 nm may be used. Preferred examples for light sources and light detectors are shown, for example, in FIG. 11.

2. Method of claim 1, wherein the sample has a volume between a volume between 0.1 μL and 15 μL, preferably between 1 μl and 15 μl, more preferably between 8 μL and 12 μL.

3. Method of aspect 1 or 2, wherein the light from the monochromatic light source is coherent and has preferably a wavelength between 350 nm and 500 nm, preferably of 405 nm, 445 nm, or 488 nm.

4. Method of any of aspects 1 to 3, wherein the monochromatic light source is a laser, preferably a diode laser, preferably a diode laser selected from the group consisting of frequency stabilized diode laser, DPSS laser, PPLN doubled diode laser, frequency multiplied DPSS laser, diode pumped fiber laser, multiplied diode pumped fiber laser, and diode pumped upconversion fiber laser.

5. Method of aspect 4, wherein the laser has a coherence length of at least 0.1 mm.

6. Method of aspect 4 or 5, wherein the laser has a power between 1 mW and 200 mW, preferably between 10 mW and 180 mW, more preferably between 50 mW and 150 mW, even more preferably between 70 mW and 120 mW, for example at 100 mW, wherein the laser is preferably a continuous wave (CW) laser and preferably not a pulsed laser.

7. Method of any of aspects 4 to 6, wherein the monochromatic light is delivered from the monochromatic light source via a at laser wavelength single mode fiber and preferably via a laser wavelength polarization maintaining single mode fiber.

8. Method of any of aspects 1 to 7, wherein light from the monochromatic light source is transmitted to the vessel with an angle φL to a longitudinal axis of the vessel, wherein φL is between 0 degrees and 45 degrees.

9. Method of aspect 8, wherein light detected with the light detector is emitted from the vessel with an angle φD to a longitudinal axis of the vessel, wherein φD is between 0 degrees and 45 degrees, wherein the value of φL is preferably identical to the value of φD.

10. Method of aspect 9, wherein an angle φS between the light that is transmitted from the monochromatic light source to the vessel and the light emitted from the vessel that is detected with the light detector is between 0 degrees and 150 degrees, preferably between 10 degrees and 150 degrees, more preferably between 10 degrees and 60 degrees.

11. Method of any of aspects 1 to 10, wherein the transmitted monochromatic light is focused in the vessel comprising the sample using an objective lens, wherein the light emitted from the vessel is preferably also focused by said objective lens, preferably wherein the objective lens has a focal length between 10 mm and 200 mm, and/or wherein the transmitted monochromatic light is focused in the vessel with a focal spot having a full width at half maximum (FWHM) between 3 μm and 30 μm, preferably resulting in a measurement volume between 0.01 nl and 0.1 nl, preferably between 0.01 nl and 0.02 nl, more preferably about 0.016 nl.

12. Method of any of aspects 1 to 11, wherein the light detector is a photomultiplier tube (PMT), a silicon photomultiplier (SiPM), or an Avalanche photodiode (APD) photon counting detector, preferably a PMT or a SiPM.

13. Method of any of aspects 1 to 12, wherein the DLS measurement is obtained in less than 5 sec, preferably in less than 1 sec.

14. Method of any of aspects 1 to 13, wherein the DLS measurement is performed only once per sample.

15. Method of any of aspects 1 to 14, wherein the DLS measurement comprises the step of performing at least one correlation operation, preferably at least one autocorrelation operation.

16. Method of any of aspects 1 to 15, wherein the DLS measurement comprises the steps of
obtaining an analog output signal obtained from the light detector; and
processing the obtained analog output signal.

17. Method of aspect 16, wherein the step of processing the obtained analog output signal comprises the step of digitalizing the obtained analog output signal into a digitalized output signal, preferably by means of an ADC.

18. Method of aspect 17, wherein the digitalized output signal is further processed with the step(s) of
i) processing the digitalized output signal as a digitalized single photon pulse signal, preferably in case the intensity of the detected light emitted from the vessel is below 2 million detected photons per second;
and/or
ii) processing the digitalized output signal as discrete values of an analog signal, preferably in case the intensity of the detected light is above 2 million detected photons per second 19. Method of aspect 18, wherein
the step of processing the output signal comprises either step i) or step ii), and wherein the time to decide whether to process the digitalized output signal as a digitalized signal according to step i) or ii) is less than 1 sec, preferably maximal 0.05 sec, preferably by using an FPGA, or
the photon counting and discrete value output signal can be processed simultaneously such that the decision whether to process according to step i) or step ii) can be met after the measurement.

20. Method of aspect 18 or 19, wherein the step of processing the obtained output signal further comprises the step(s) of
storing the processed digitalized output signal obtained from step i) or step ii); or
storing the processed digitalized output signals obtained from step i) and step ii); and
further processing one of the stored output signals.

21. Method of any of aspects 1 to 20, the method further comprising the step of
measuring fluorescence, preferably of said particles in solution comprised in the sample and/or of the material of the vessel, wherein said fluorescence is preferably an autofluorescence of said particles and/or of the material of the vessel, and/or
measuring back-reflection of the vessel comprising the sample.
As mentioned above, for said fluorescence and/or back-reflection measurements, additional light source(s) and/or additional light detector(s) may be used.

22. Method of aspect 21, the method further comprising the steps of
determining the position of the vessel based on the measured fluorescence and/or based on the measured back-reflection, and
optionally positioning the vessel based on the measured fluorescence/back-reflection and the determined vessel position.

23. Method of any of aspects 1 or 22, the method further comprising the step of
tempering the vessel over time at least with a first temperature at a first time point and a second temperature at a second time point.

24. Method of aspect 23, wherein the step of tempering the vessel over time at least with a first temperature at a first time point and a second temperature at a second time point comprises tempering the vessel with a tempering rate between 0.01° C. per minute and 30° C. per minute, preferably between 0.1° C. per minute and 10° C. per minute, and/or wherein the first temperature and the second temperature are between −20° C. and 160° C.

25. Method of any of aspects 1 to 24, the method further comprising the step(s) of
performing a nano differential scanning fluorimetry (nano-DSF) measurement; and/or
measuring back-reflection of the vessel comprising the sample.

26. Method of any of aspects 1 to 25, further comprising the steps of
providing a further light detector, and
measuring static scattering light of the vessel comprising the sample using the further light detector, preferably with an angle $\varphi$ to a longitudinal axis of the vessel, wherein $\varphi$ is preferably between 10 degrees and 150 degrees, more preferably between 10 degrees and 60 degrees.

27. Method of any of aspects 1 to 26, wherein the vessel is a capillary and/or multi-well plate, preferably a glass capillary with a round cross-section and an inner diameter between 0.1 mm and 1 mm, preferably between 0.15 mm and 0.5 mm, and preferably an outer diameter between 0.2 mm and 1.2 mm, preferably between 0.65 mm and 1 mm and a length between 5 mm and 70 mm, preferably between 32 mm and 50 mm, more preferably of about 50 mm.

28. Method of any of aspects 1 to 27, wherein a plurality of vessels is provided, wherein each vessel comprises a sample of particles in solution, and wherein characteristics of particles in solution are measured for each vessel according to any of aspects 1 to 27.

29. Method of aspect 28, wherein
a fluorescence measurement for each vessel is followed by a DLS measurement for each vessel; or
a DLS measurement for each vessel is followed by a fluorescence measurement for each vessel; or
a fluorescence measurement and a DLS measurement is performed for one vessel of the plurality of vessels followed by a fluorescence measurement and a DLS measurement for another vessel of the plurality of vessels.

30. Method of any of aspects 1 to 29, wherein the characteristics are selected from the group consisting of particle size distribution, aggregation temperature, melting temperature, transition temperature, unfolding temperature onset, temperature of liquid-liquid phase separation ($T_{LLPS}$) free folding energy, second virial coefficient ($B_{22}$), self-interactions of particles, colloidal stability, hydrodynamic radius, repulsive or attractive interaction between particles ($K_D$), solubility, long-term protein stability and critical denaturant concentrations.

31. A device for detecting characteristics of particles in solution, preferably in accordance with any of aspects 1 to 30, wherein said device comprises:

means for accommodating at least one vessel comprising a sample of said particles in solution, preferably for accommodating between 0.1 to 15 µL of said particles;

a monochromatic light source and a light detector;

means for performing a DSL measurement; and control means adapted for controlling the means for accommodating at least one vessel;

controlling the monochromatic light source for transmitting light from the monochromatic light source to the at least one vessel;

controlling the light detector for detecting signals from the at least one vessel; and controlling said means for performing a DSL measurement.

32. The device of aspect 31, wherein said device further comprises:

means for performing a correlation operation, preferably an autocorrelation operation, wherein said autocorrelation operation is preferably an autocorrelation logic embodied in hardware and/or software; and 33. The device of aspect 31 or 32, wherein said device further comprises:

means for digitalizing signals obtained from the light detector, wherein said means preferably comprise a field programmable gate array (FPGA), wherein the control means are further adapted for controlling said means for digitalizing signals obtained from the light detector.

34. The device of any of aspects 31 to 33, wherein said device further comprises:

means for measuring the fluorescence of said particles in solution comprised in the sample, wherein the control means are further adapted for controlling said means for measuring the fluorescence of said particles in solution comprised in the sample.

As mentioned above, it is preferred to provide an additional light source for the fluorescence measurement, e.g., providing an LED with a (short or shorter) excitation wavelength, e.g. at 280 nm. For the fluorescence measurement it is further preferred to provide an additional light detector, preferably two additional light detectors for the fluorescence measurement, e.g., for detecting light at a long or longer wavelength (with respect to the excitation wavelength), e.g., one or two detectors to detect light at about 330 nm and 350 nm.

35. The device of any of aspects 31 to 34, wherein said device further comprises:

positioning means for positioning the means for accommodating the sample of said particles in solution, wherein the control means are further adapted for controlling the positioning means for accommodating the sample.

36. The device of any of aspects 31 to 35, wherein said device further comprises:

a temperature control system for tempering the vessel over time at least with a first temperature at a first time point and a second temperature at a second time point, wherein the control means are further adapted for controlling said temperature control system for tempering the vessel over time at least with a first temperature at a first time point and a second temperature at a second time point.

37. The device of any of aspects 31 to 36, wherein said device further comprises:

means for performing a nano-DSF measurement and/or means for measuring back-reflection, wherein the control means are further adapted for controlling said means for performing a nano-DSF measurement and/or said means for measuring back-reflection.

As mentioned above, it is preferred to provide an additional light source for the back-reflection measurement, e.g., providing an LED with an excitation wavelength of 385 nm. For the back-reflection measurement it is further preferred to provide an additional light detector, e.g., for detecting back-reflected light at 385 nm.

38. The device of any of aspects 31 to 37, wherein said device further comprises:

a further light detector; and means for performing a static scattering light measurement, wherein the control means are further adapted for controlling said means for performing a static scattering light measurement.

39. The device of any of aspects 31 to 38, wherein said device further comprises:

a single mode fiber; and means for delivering monochromatic light from the monochromatic light source via said single mode fiber, wherein the control means are further adapted for controlling said means for delivering monochromatic light from the monochromatic light source via said single mode fiber.

LIST OF REFERENCE SIGNS

10: Longitudinal axis of a vessel, e.g. longitudinal axis of a capillary

11: Vessel, e.g. capillary

12: Sample comprising the particles in solution under study

13: Tempering element, e.g., a heating pad/bed

14: Fluorescence optics

15: DLS optics

16: Fluorescence focus

17: DLS focus

18: x-distance between fluorescence focus and DLS focus

19: Reflected beams

20: Angle between capillary axis and detected light beam ($\varphi_D$)

30: Light detector, e.g. a DLS detector

31: ADC (Analog to Digital Converter)

32: Pulse discriminator

33: Correlator

34: FPGA

35: PC

36: Photon counting threshold value

38: digitalized output signal as digital photon pulse signal

39: digitalized output signal of PMT

50: Excitation beam

51: Detected beams

52: Objective lens (or objective mirror)

53: Angle between capillary axis and excitation light beam ($\varphi_L$)

53': Angle between capillary axis and excitation light beam ($\varphi_L$) depicted as $\varphi_L$-90 degrees

54: Angle between excitation light beam and detected light beam ($\varphi_S$)

55: Monochromatic light source, e.g. a laser

56: Collimating lens

57: Optical fiber (single mode, alternatively polarization-preserving, or multi-mode)

58: Beam splitter power, e.g. 50:50

59: Beam splitter wavelength, e.g. low pass 620 nm

60: Dichroic filter, e.g. bandpass 405/5 nm to block fluorescence

61: Polarization filter

62: Optics to improve the beam quality of the laser

63: Aperture to reduce stray light

64: Cylindrical lens for correction of capillary astigmatism

The invention claimed is:

1. Method to measure characteristics of particles in solution, said method comprising the steps of:

providing a vessel comprising a sample of said particles in solution;

providing a monochromatic light source and a light detector;

transmitting light from the monochromatic light source to the vessel comprising the sample;

detecting light emitted from the vessel with the light detector; and determining characteristics of said particles in solution comprised in the sample based on a dynamic light scattering (DLS) measurement, wherein the DLS measurement comprises the steps of obtaining an analog output signal obtained from the light detector; and processing the obtained analog output signal, wherein the step of processing the obtained analog output signal comprises the step of digitalizing the obtained analog output signal into a digitalized output signal, wherein the digitalized output signal is further processed with the step(s) of i) processing the digitalized output signal as a digitalized single photon pulse signal, in case an intensity of the light detected by the light detector is below a predetermined number of detected photons per second; and/or ii) processing the digitalized output signal as discrete values of an analog signal, in case the intensity of the light detected by the light detector is above said predetermined number of detected photons per second.

2. Method of claim 1, wherein the vessel is a capillary and/or multi-well plate.

3. Method of claim 1, the method further comprising the step of measuring fluorescence, and/or measuring back-reflection of the vessel comprising the sample.

4. Method of claim 3, the method further comprising the steps of determining a position of the vessel based on the measured fluorescence and/or based on the measured back-reflection, and optionally positioning the vessel based on the measured fluorescence and/or back-reflection and the determined vessel position.

5. Method of claim 1, wherein the light from the monochromatic light source is coherent.

6. Method of claim 1, wherein the monochromatic light source is a laser.

7. Method of claim 6, wherein the laser has a coherence length of at least 0.1 mm.

8. Method of claim 1, wherein the DLS measurement is obtained in less than 5 sec.

9. Method of claim 1, wherein the vessel has a volume between 0.1 μL and 15 μL.

10. Method of claim 1, wherein light from the monochromatic light source is transmitted to the vessel with an angle φL to a longitudinal axis of the vessel, wherein φL is between 0 degrees and 45 degrees.

11. Method of claim 10, wherein light detected with the light detector is emitted from the vessel with an angle φD to a longitudinal axis of the vessel, wherein φD is between 0 degrees and 45 degree.

12. Method of claim 11, wherein an angle φS between the light that is transmitted from the monochromatic light source to the vessel and the light emitted from the vessel that is detected with the light detector is between 0 degrees and 150 degrees.

13. Method of claim 1, wherein the transmitted monochromatic light is focused in the vessel comprising the sample using an objective lens.

14. Method of claim 1, wherein the light detector is a photomultiplier tube (PMT), a silicon photomultiplier (SiPM), or an Avalanche photodiode (APD) photon counting detector.

15. Method of claim 1, wherein the DLS measurement is performed only once per sample.

16. Method of claim 1, wherein the DLS measurement comprises the step of performing at least one correlation operation.

17. Method of claim 1, wherein the digitalized output signal is further processed with the step(s) of i) processing the digitalized output signal as a digitalized single photon pulse signal in case the intensity of the detected light emitted from the vessel is below 2 million detected photons per second; and/or ii) processing the digitalized output signal as discrete values of an analog signal in case the intensity of the detected light is above 2 million detected photons per second.

18. Method of claim 17, wherein the step of processing the digitalized output signal comprises either step i) or step ii), and wherein the time to decide whether to process the digitalized output signal as a digitalized output signal according to step i) or ii) is less than 1 sec or a photon counting and analog output signal can be processed simultaneously such that the decision whether to process according to step i) or step ii) can be met after the DLS measurement.

19. Method of claim 17, wherein the step of processing the obtained analog output signal further comprises the step(s) of storing the processed digitalized output signal obtained from step i) or step ii); or storing the processed digitalized output signals obtained from step i) and step ii); and further processing one of the stored output signals.

20. Method of claim 1, the method further comprising the step of tempering the vessel over time at least with a first temperature at a first time point and a second temperature at a second time point.

21. Method of claim 20, wherein the step of tempering the vessel over time at least with a first temperature at a first time point and a second temperature at a second time point comprises tempering the vessel with a tempering rate between 0.01° C. per minute and 30° C. per minute.

22. Method of claim 1, the method further comprising the step(s) of performing a nano differential scanning fluorimetry (nano-DSF) measurement; and/or measuring back-reflection of the vessel comprising the sample.

23. Method of claim 1, further comprising the steps of providing a further light detector, and measuring static scattering light of the vessel comprising the sample using the further light detector.

24. Method of claim 1, wherein a plurality of vessels is provided, wherein each vessel comprises a sample of particles in solution, and wherein characteristics of particles in solution are measured for each vessel.

25. Method of claim 24, wherein a fluorescence measurement for each vessel is followed by a DLS measurement for each vessel; or a DLS measurement for each vessel is followed by a fluorescence measurement for each vessel; or a fluorescence measurement and a DLS measurement is performed for one vessel of the plurality of vessels followed by a fluorescence measurement and a DLS measurement for another vessel of the plurality of vessels.

26. Method of claim 1, wherein the characteristics are selected from the group consisting of particle size distribution, aggregation temperature, melting temperature, transition temperature, unfolding temperature onset, temperature of liquid-liquid phase separation ($T_{LLPS}$) free folding energy, second virial coefficient ($B_{22}$), self-interactions of particles, colloidal stability, hydrodynamic radius, repulsive or attractive interaction between particles ($K_D$), solubility, long-term protein stability and critical denaturant concentrations.

27. A device for detecting characteristics of particles in solution according to the method recited in claim 1, wherein said device comprises:

means for accommodating at least one vessel comprising a sample of said particles in solution;

a monochromatic light source and a light detector;

means for performing a DSL measurement; and control means adapted for controlling the means for accommodating at least one vessel;

controlling the monochromatic light source for transmitting light from the monochromatic light source to the at least one vessel;

controlling the light detector for detecting signals from the at least one vessel; and controlling said means for performing a DSL measurement.

28. The device of claim 27, wherein said device further comprises:

means for performing a correlation operation.

29. The device of claim 27, wherein said device further comprises:

means for digitalizing signals obtained from the light detector wherein the control means are further adapted for controlling said means for digitalizing signals obtained from the light detector.

30. The device of claim 27, wherein said device further comprises:

means for measuring the fluorescence of said particles in solution comprised in the sample, wherein the control means are further adapted for controlling said means for measuring the fluorescence of said particles in solution comprised in the sample.

31. The device of claim 27, wherein said device further comprises:

positioning means for positioning the means for accommodating at least one vessel comprising the sample of said particles in solution, wherein the control means are further adapted for controlling the positioning means.

32. The device of claim 27, wherein said device further comprises:

a temperature control system for tempering the at least one vessel over time at least with a first temperature at a first time point and a second temperature at a second time point, wherein the control means are further adapted for controlling said temperature control system.

33. The device of claim 27, wherein said device further comprises:

means for performing a nano-DSF measurement and/or means for measuring back-reflection, wherein the control means are further adapted for controlling said means for performing a nano-DSF measurement and/or said means for measuring back-reflection.

34. The device of claim 27, wherein said device further comprises:

a further light detector; and means for performing a static scattering light measurement, wherein the control means are further adapted for controlling said means for performing a static scattering light measurement.

35. The device of claim 27, wherein said device further comprises:

a single mode fiber; and means for delivering monochromatic light from the monochromatic light source via said single mode fiber, wherein the control means are further adapted for controlling said means for delivering monochromatic light from the monochromatic light source via said single mode fiber.

* * * * *